(12) United States Patent  
Fukumoto et al.

(10) Patent No.: US 8,740,796 B2  
(45) Date of Patent: Jun. 3, 2014

(54) ULTRASONIC DIAGNOSTIC DEVICE, AND METHOD FOR MEASURING INTIMA-MEDIA THICKNESS

(75) Inventors: Takenori Fukumoto, Kanagawa (JP); Kazuya Takagi, Osaka (JP); Takao Suzuki, Kanagawa (JP); Akihiro Kawabata, Kanagawa (JP)

(73) Assignee: Konica Minolta, Inc., Tokyo (JP)

( * ) Notice: Subject to any disclaimer, the term of this patent is extended or adjusted under 35 U.S.C. 154(b) by 37 days.

(21) Appl. No.: 13/520,214

(22) PCT Filed: Nov. 12, 2010

(86) PCT No.: PCT/JP2010/006658  
§ 371 (c)(1),  
(2), (4) Date: Jul. 2, 2012

(87) PCT Pub. No.: WO2011/099102  
PCT Pub. Date: Aug. 18, 2011

(65) Prior Publication Data  
US 2012/0310086 A1  Dec. 6, 2012

(30) Foreign Application Priority Data  
Feb. 10, 2010 (JP) .................. 2010-027245

(51) Int. Cl.  
*A61B 8/00* (2006.01)  
*G06K 9/00* (2006.01)

(52) U.S. Cl.  
USPC ........................... 600/437; 600/450; 382/128

(58) Field of Classification Search  
USPC .................. 600/437, 449, 450, 485; 382/128  
See application file for complete search history.

(56) References Cited

U.S. PATENT DOCUMENTS 6,132,373 A   10/2000   Ito et al.

| 2005/0228278 A1 | 10/2005 | Chalana et al. |
| 2007/0165916 A1 | 7/2007 | Cloutier et al. |
| 2008/0125651 A1 | 5/2008 | Watanabe et al. |
| 2008/0171939 A1 | 7/2008 | Ishihara |
| 2009/0279753 A1 | 11/2009 | Sakaida |
| 2010/0063391 A1 | 3/2010 | Kanai et al. |

FOREIGN PATENT DOCUMENTS

| JP | 11-000327 A | 1/1999 |
| JP | 11-318896 A | 11/1999 |
| JP | 2005-534462 T | 11/2005 |
| JP | 2007-512862 T | 5/2007 |

(Continued)

OTHER PUBLICATIONS

International Search Report for corresponding International Application No. PCT/JP2010/006658 mailed Jan. 11, 2011.

(Continued)

*Primary Examiner* — Michael Rozanski  
(74) *Attorney, Agent, or Firm* — Lucas & Mercanti, LLP

(57) ABSTRACT

An ultrasonic diagnostic apparatus transmits an ultrasonic wave toward a body and obtains biological information based on an echo signal received and includes: an intensity distribution generating section that generates an echo intensity distribution in a depth direction about a vascular wall based on the echo signal; a template generating section that generates a template to detect a boundary based on template data provided in advance to represent a reference pattern of the intensity distribution; a pattern similarity calculating section that changes the depth and intima-media thickness pattern of the template to calculate similarity between the template and the intensity distribution on any change made; and a boundary defining section that defines lumen and adventitia boundaries based on the degree of similarity calculated on any change made. The intima-media thickness is thus determined without depending on the magnitudes of echo intensity variations on the lumen and adventitia sides.

28 Claims, 19 Drawing Sheets

(56) References Cited

FOREIGN PATENT DOCUMENTS

| | | |
|---|---|---|
| JP | 2008-006188 A | 1/2008 |
| JP | 2008-161220 A | 7/2008 |
| JP | 2008-168016 A | 7/2008 |
| WO | 2005/002446 A1 | 1/2005 |
| WO | 2008/023618 A1 | 2/2008 |

OTHER PUBLICATIONS

PCT/ISA/237 for corresponding International Application No. PCT/JP2010/006658 mailed Jan. 11, 2011 and partial English translation.

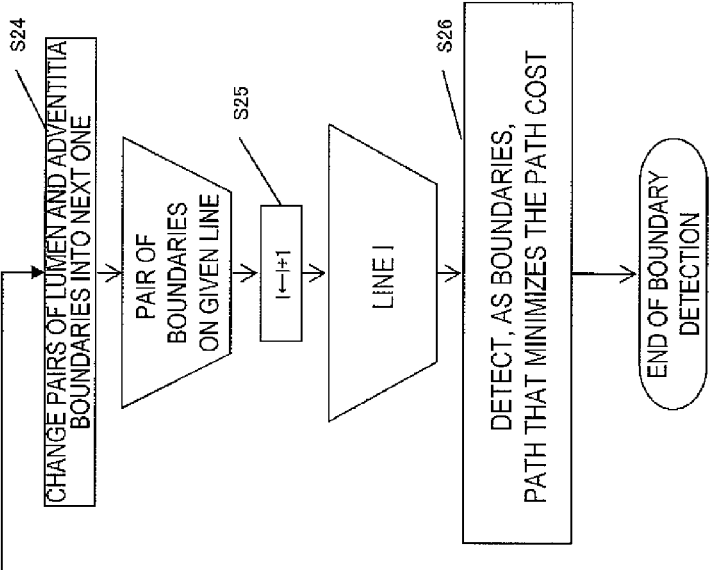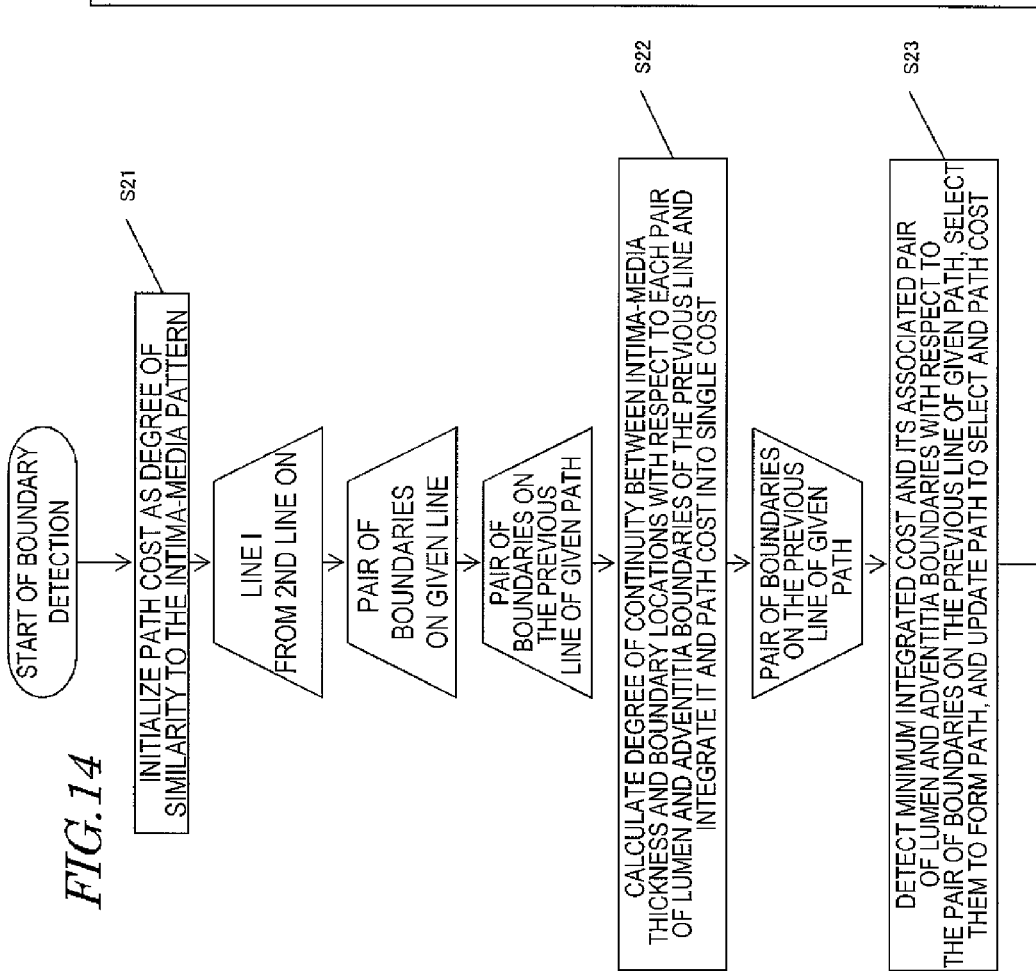
FIG. 14

ULTRASONIC DIAGNOSTIC DEVICE, AND METHOD FOR MEASURING INTIMA-MEDIA THICKNESS

TECHNICAL FIELD

The present invention relates to an ultrasonic diagnostic apparatus for calculating the thickness of the intima-media complex of a blood vessel such as a carotid artery.

BACKGROUND ART

Diagnosis of an arterial sclerosis is carried out using an ultrasonic diagnostic apparatus that transmits an ultrasonic wave toward a body and obtains biological information based on an echo signal that has been received from the body. In making a diagnosis of arterial sclerosis, the intima-media complex thickness of a carotid artery is known as one of most important indices to the status of an initial atheroma sclerosis. The "intima-media complex" or "intima-media" is a generic term collectively referring to the intima and the media of a vascular wall that are present between the lumen and adventitia of a blood vessel. The intima-media complex thickness or intima-media thickness is generally called, and will also be referred to herein as, "IMT".

FIG. 1 illustrates an intima-media 3 that is present between the lumen 1 and adventitia 2 of a blood vessel. In making an inspection, a lumen boundary 4, which is the boundary between the lumen 1 and intima of the blood vessel, and an adventitia boundary 5, which is the boundary between the media and the adventitia 2, are detected and have their thicknesses measured. The technique disclosed in Patent Document No. 1 is known as a method for measuring the IMT automatically.

FIG. 2 shows the intensity distribution of an echo for use to define the adventitia boundary and the lumen boundary according to the technique disclosed in Patent Document No. 1. As shown in FIG. 2, according to the method disclosed in Patent Document No. 1, two portions of the echo intensity distribution in the depth direction, of which the intensity variations are equal to or greater than a predetermined value, are regarded as potential candidates for boundaries, and the bigger one of the two is defined to be the adventitia boundary and the smaller one is defined to be the lumen boundary.

CITATION LIST

Patent Literature

Patent Document No. 1: Japanese Patent Application Laid-Open Publication No. 2008-168016

SUMMARY OF INVENTION

Technical Problem

According to the method of Patent Document No. 1, however, stereotyped processing is carried out depending on just the magnitude of the intensity variation, and therefore, the IMT could not be measured correctly.

The intensity variation of the lumen boundary could be greater than that of the adventitia boundary as shown in FIG. 3. This is an example indicating that a region with the greater intensity variation is not always the adventitia boundary.

If the method disclosed in Patent Document No. 1 is applied to such a situation, the lumen boundary will be taken for the adventitia boundary and the IMT cannot be measured properly.

It is therefore an object of the present invention to detect the lumen boundary and the adventitia boundary correctly and measure the IMT accurately without depending on the magnitudes of echo intensity variations on the lumen and adventitia sides.

Solution to Problem

An ultrasonic diagnostic apparatus according to the present invention transmits an ultrasonic wave toward a body and obtains biological information based on an echo signal that has been received from the body. The apparatus includes: an intensity distribution generating section, which generates an echo intensity distribution in a depth direction with respect to a vascular wall based on the echo signal; a template generating section, which generates a template for use to detect a boundary based on another template that has been provided in advance to represent a reference pattern of the echo intensity distribution; a pattern similarity calculating section, which changes the level of the template in the depth direction and a pattern of the template representing an intima-media thickness to calculate the degree of similarity between the template and the intensity distribution on any change made in the level or pattern of the template; and a boundary defining section, which defines a lumen boundary and an adventitia boundary based on the degree of similarity that has been calculated on any change made in the level or pattern of the template.

Another ultrasonic diagnostic apparatus according to the present invention includes: an intensity distribution generating section, which generates an echo intensity distribution in a depth direction with respect to a vascular wall based on the echo signal; a template generating section, which generates a template for use to detect a boundary based on another template that has been provided in advance to represent a reference pattern of the echo intensity distribution; a pattern similarity calculating section, which changes a pattern of the template representing an intima-media thickness with respect to each of multiple different combinations of candidate boundaries that are located at mutually different levels in the depth direction to calculate the degree of similarity between the template and the intensity distribution on any change made in the pattern of the template; a boundary continuity calculating section, which calculates, with respect to the combination selected in association with multiple adjacent acoustic lines, the degree of continuity between the boundaries based on a difference between the intensity values of the echo signals of the respective acoustic lines; a boundary estimating section, which generates an estimated value by integrating together the pattern similarity and the boundary continuity with respect to the combination; and a boundary defining section, which defines a lumen boundary and an adventitia boundary based on the integrated estimated value.

The template generated by the template generating section may include at least three regions, one or more of which is a variable-length region with a variable range length.

The at least three regions may be arranged in order, and the variable-length region may be the middle one of the at least three regions.

One of the at least three regions that is located at one end may correspond to a low-echo tissue region and another one of the at least three regions that is located at the other end may correspond to a high-echo tissue region.

The low-echo tissue region may correspond to a blood flow region and the high-echo tissue region may correspond to the adventitia wall of a blood vessel and a body tissue.

The variable-length region may correspond to an intima-media region of the blood vessel.

The pattern similarity calculating section may calculate the degree of similarity by normalizing the length of the variable-length region.

The pattern similarity calculating section may normalize the length of the variable-length region by using the average intensity of the variable-length region as its intensity.

The template generated by the template generating section may be made up of two kinds of sub-templates, each of which is formed of at least two regions, and the two kinds of templates may have a variable distance between themselves. The pattern similarity calculating section may calculate two degrees of similarity using the two kinds of sub-templates and may then combine and integrate the two degrees of similarity together to obtain the degree of similarity.

The two regions that form each of the two kinds of templates may correspond to a low-echo tissue region and a high-echo tissue region, respectively.

The low- and high-echo tissue regions of the two kinds of templates respectively may correspond to either a blood flow region and an intima-media region or a lumen boundary and a predetermined tissue region that may include an adventitia boundary, an arterial adventitia wall and a body tissue.

The template generating section may change the coefficient value of the template to generate according to the contrast of the intensity distribution that has been generated by the intensity distribution generating section.

The degree of similarity estimated by the pattern similarity calculating section may be defined by an intensity difference between boundaries as specified by the template that has been generated by the template generating section.

The degree of similarity estimated by the pattern similarity calculating section may be defined by a normalized correlation between the template that has been generated by the template generating section and the intensity distribution that has been generated by the intensity distribution generating section.

The ultrasonic diagnostic apparatus may further include a posterior wall detecting section that detects a high-echo region based on the intensity distribution that has been generated by the intensity distribution generating section. The boundary defining section may set the boundaries only within the posterior wall range detected.

The high-echo region detected by the posterior wall detecting section may correspond to a vascular wall.

The boundary estimating section may calculate the estimated value by dynamic programming.

The boundary estimating section may calculate the estimated value by using an intensity distribution with a decreased resolution. The boundary defining section may tentatively choose candidates based on the intensity distribution with the decreased resolution and may then define the lumen boundary and the adventitia boundary in a region surrounding the tentatively chosen candidates based on the intensity distribution with the original resolution.

The boundary estimating section may calculate the estimated value in an acoustic line direction with the candidates narrowed down, by dynamic programming, to ones that have either good estimated values or a predetermined estimated value.

The boundary continuity calculating section may calculate the degree of continuity between boundaries, which is defined by a level difference between the boundaries in the acoustic line direction.

The pattern similarity calculating section, the boundary continuity calculating section, the boundary estimating section and the boundary defining section may screen the potential boundary candidates for the lumen boundary and the adventitia boundary, and the boundary defining section may define the lumen boundary and the adventitia boundary at the same time.

The boundary continuity calculating section may calculate the degree of continuity between the boundaries, which is defined as a thickness difference to be determined by the levels of the lumen and adventitia boundaries in the acoustic line direction.

If the pattern similarity calculating section calculates the degree of similarity while the boundary defining section is setting the lumen and adventitia boundaries in a predetermined order and when the level of one of the two boundaries has not been determined yet, the pattern similarity calculating section may fix the other boundary, may calculate the degrees of similarity with respect to a template that has multiple thicknesses associated with the level of the one boundary, and may define either the maximum value or the average value of the degrees of similarity calculated to be the degree of similarity of the other boundary.

The boundary defining section may compare an estimated value that has been used to detect a lumen boundary and then an adventitia boundary with the candidates narrowed down to ones under the lumen boundary to an estimated value that has been used to detect the adventitia boundary and then the lumen boundary with the candidates narrowed down to ones over the adventitia boundary, and may finally adopt a boundary that has been detected with the better estimated value.

The ultrasonic diagnostic apparatus may further include an IMT calculating section that calculates the thickness of an intima-media based on the levels of the lumen and adventitia boundaries.

An intima-media thickness measuring method according to the present invention is designed to measure the intima-media thickness of a vascular wall based on an echo signal that has been received from a body in response to an ultrasonic wave that has been transmitted toward him or her. The method includes the steps of: generating an echo intensity distribution in a depth direction with respect to the vascular wall based on the echo signal; generating a template for use to detect a boundary based on another template that has been provided in advance to represent a reference pattern of the echo intensity distribution; changing the level of the template in the depth direction and a pattern of the template representing the intima-media thickness to calculate the degree of similarity between the template and the intensity distribution on any change made in the level or pattern of the template; defining a lumen boundary and an adventitia boundary based on the degree of similarity that has been calculated on any change made in the level or pattern of the template; and calculating the intima-media thickness based on the lumen and adventitia boundaries that have been defined.

Another intima-media thickness measuring method according to the present invention is designed to measure the intima-media thickness of a vascular wall based on an echo signal that has been received from a body in response to a ultrasonic wave that has been transmitted toward him or her. The method includes the steps of: generating an echo intensity distribution in a depth direction with respect to the vascular wall based on the echo signal; generating a template for use to detect a boundary based on another template that has been provided in advance to represent a reference pattern of the echo intensity distribution; changing a pattern of the template representing the intima-media thickness for each of multiple different combinations of candidate boundaries that are located at mutually different levels in the depth direction to calculate the degree of similarity between the template and the intensity distribution on any change made in the pattern of the template; calculating, with respect to the combination selected in association with multiple adjacent acoustic lines, the degree of continuity between the boundaries based on a difference between the intensity values of the echo signals of the respective acoustic lines; generating an estimated value by integrating together the pattern similarity and the boundary continuity with respect to the combination; defining a lumen boundary and an adventitia boundary based on the integrated estimated value; and calculating the intima-media thickness based on the lumen and adventitia boundaries that have been defined.

Advantageous Effects of Invention

According to the present invention, the lumen boundary and the adventitia boundary are detected as a set, not independently of each other, and therefore, the IMT can be measured accurately even if the intensity variation of the lumen boundary is greater than that of the adventitia boundary.

Figure 6:
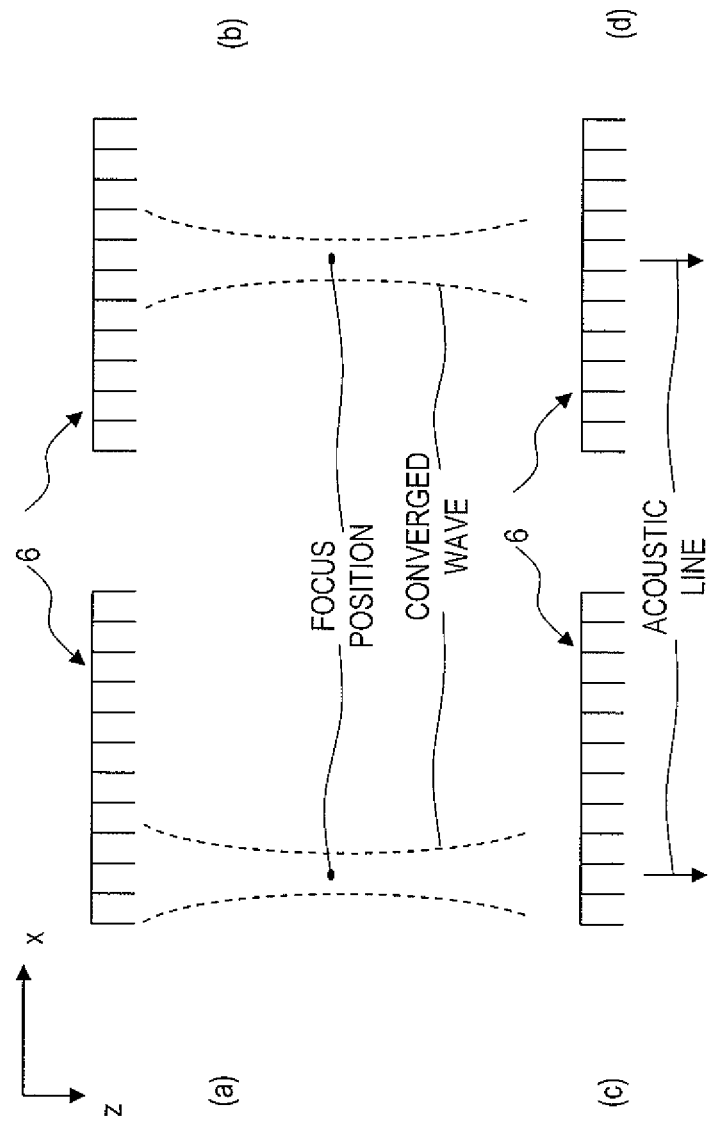

Portions (a) and (b) of FIG. 6 are schematic representations illustrating ultrasonic converged waves in a situation where a focus position is formed by a number of ultrasonic transducers that are arranged in the x direction and portions (c) and (d) illustrate simplified versions of the ultrasonic converged waves.

Figure 7:
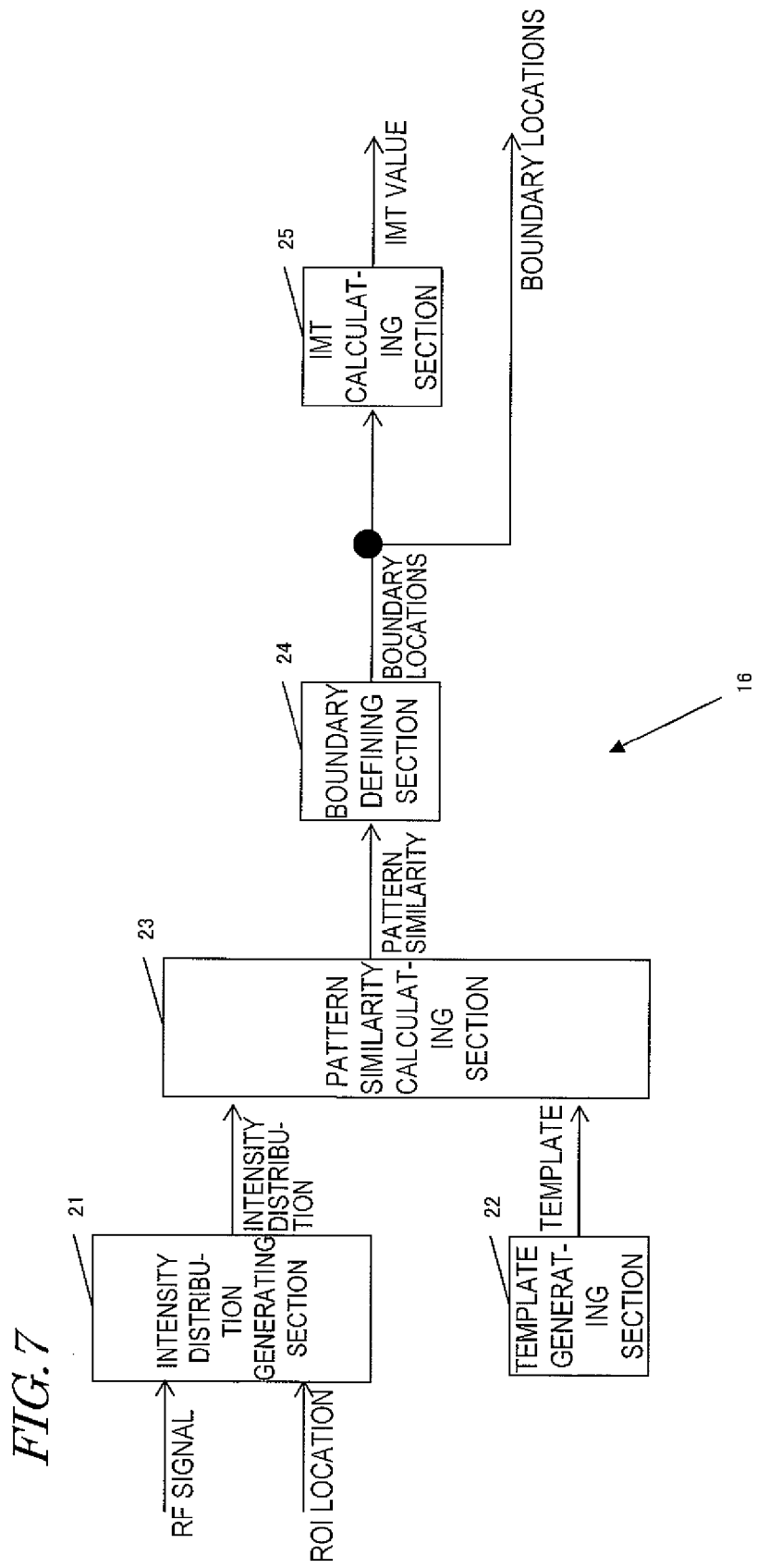

FIG. 7 is a block diagram illustrating a configuration for an IMT measuring section 16.

Figure 8:
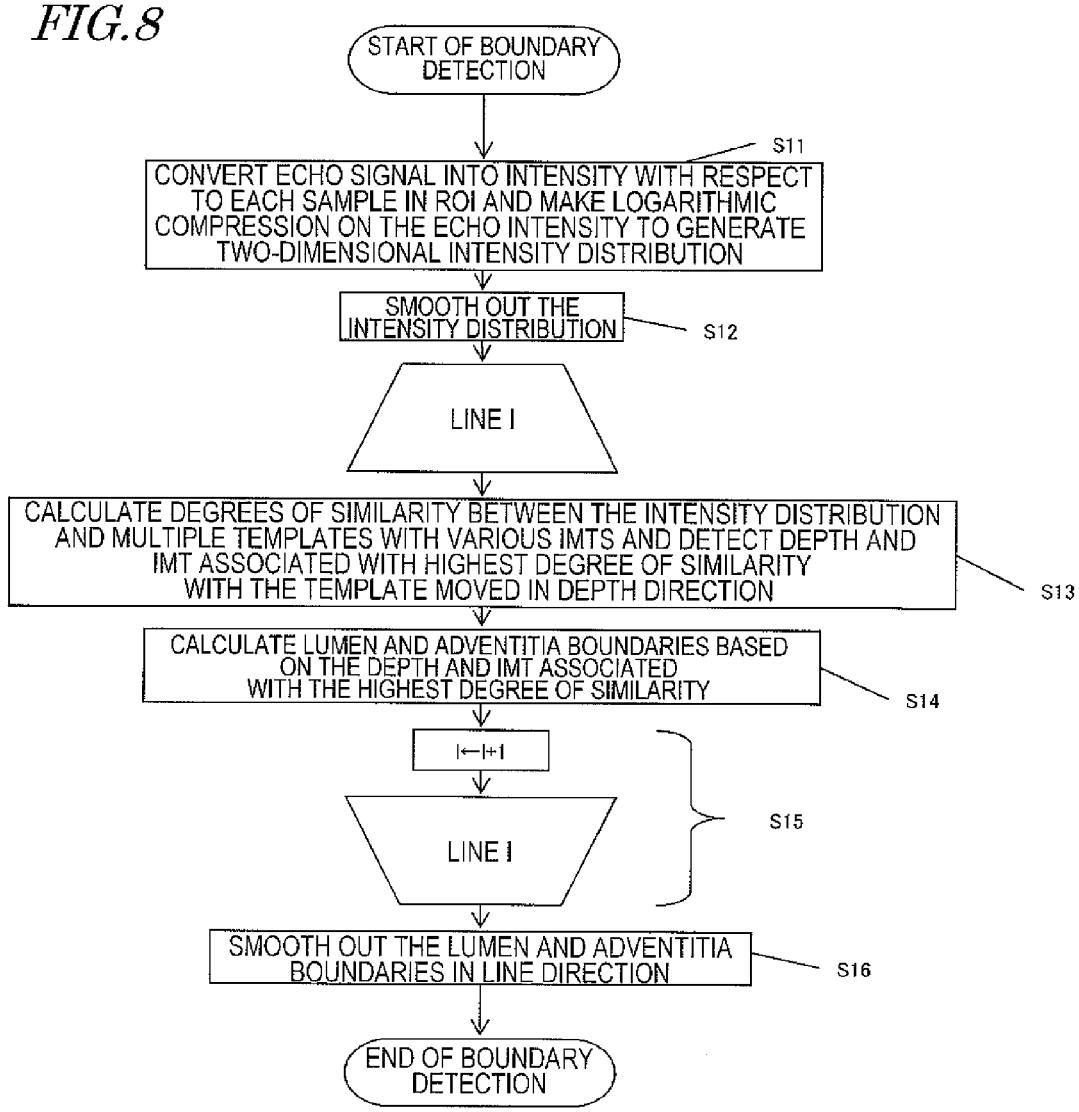

FIG. 8 is a flowchart showing the procedure of IMT calculation processing.

Figure 9:
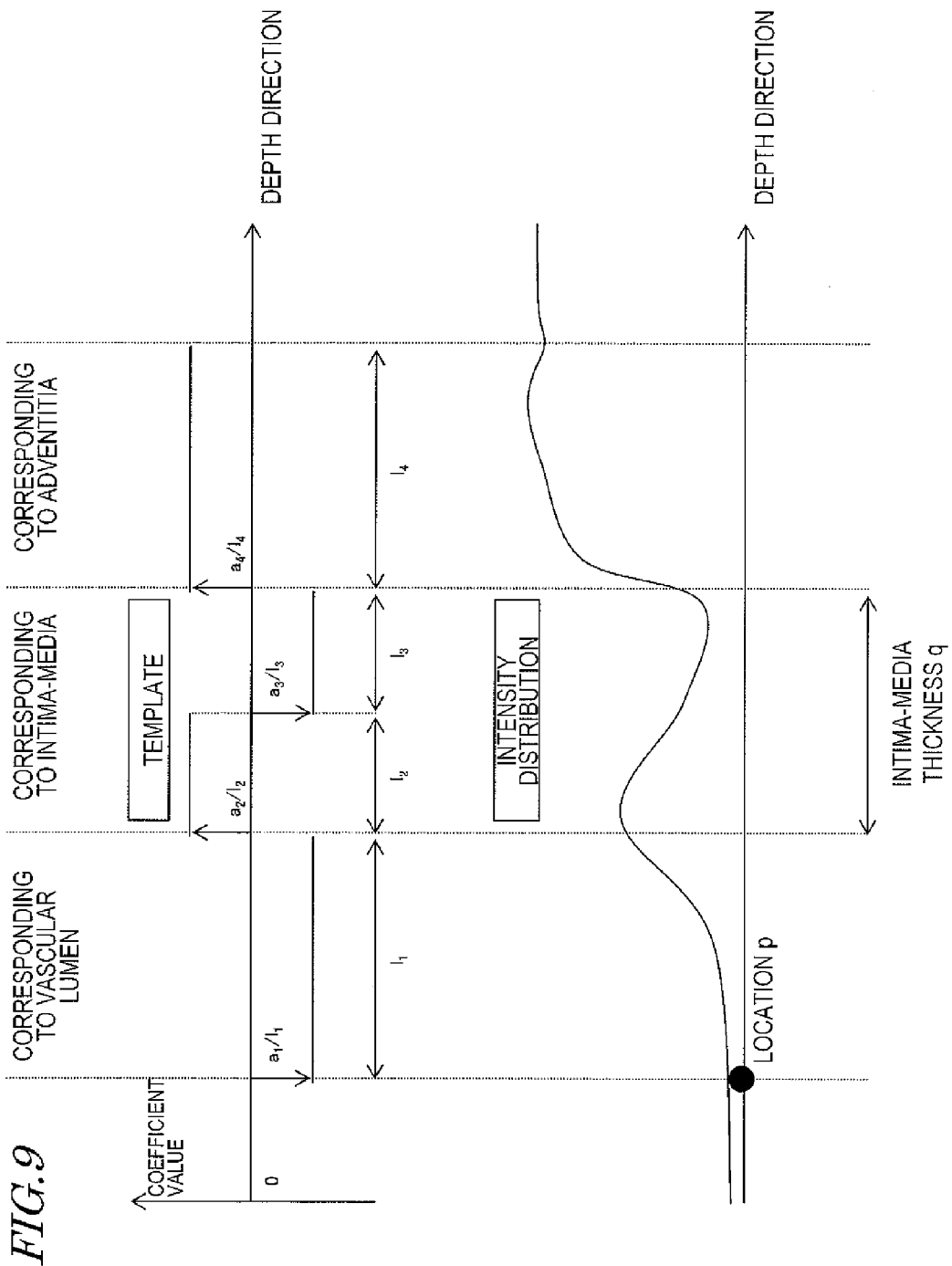

FIG. 9 shows a coefficient pattern (intima-media pattern).

Figure 10:
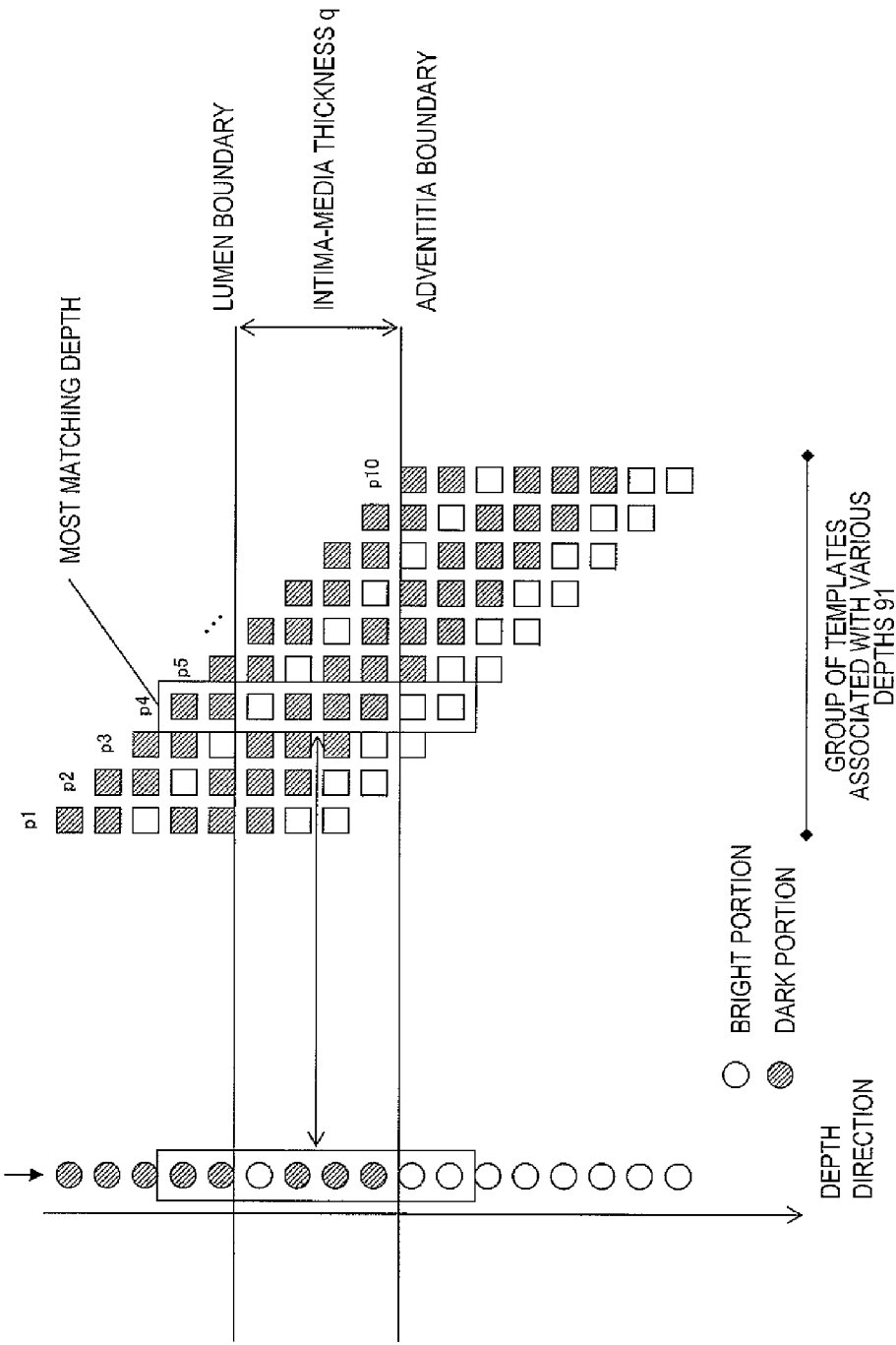

FIG. 10 illustrates the intensity distribution 90 of a given acoustic line (or line) and a group 91 of templates that are associated with various depths.

Figure 11:
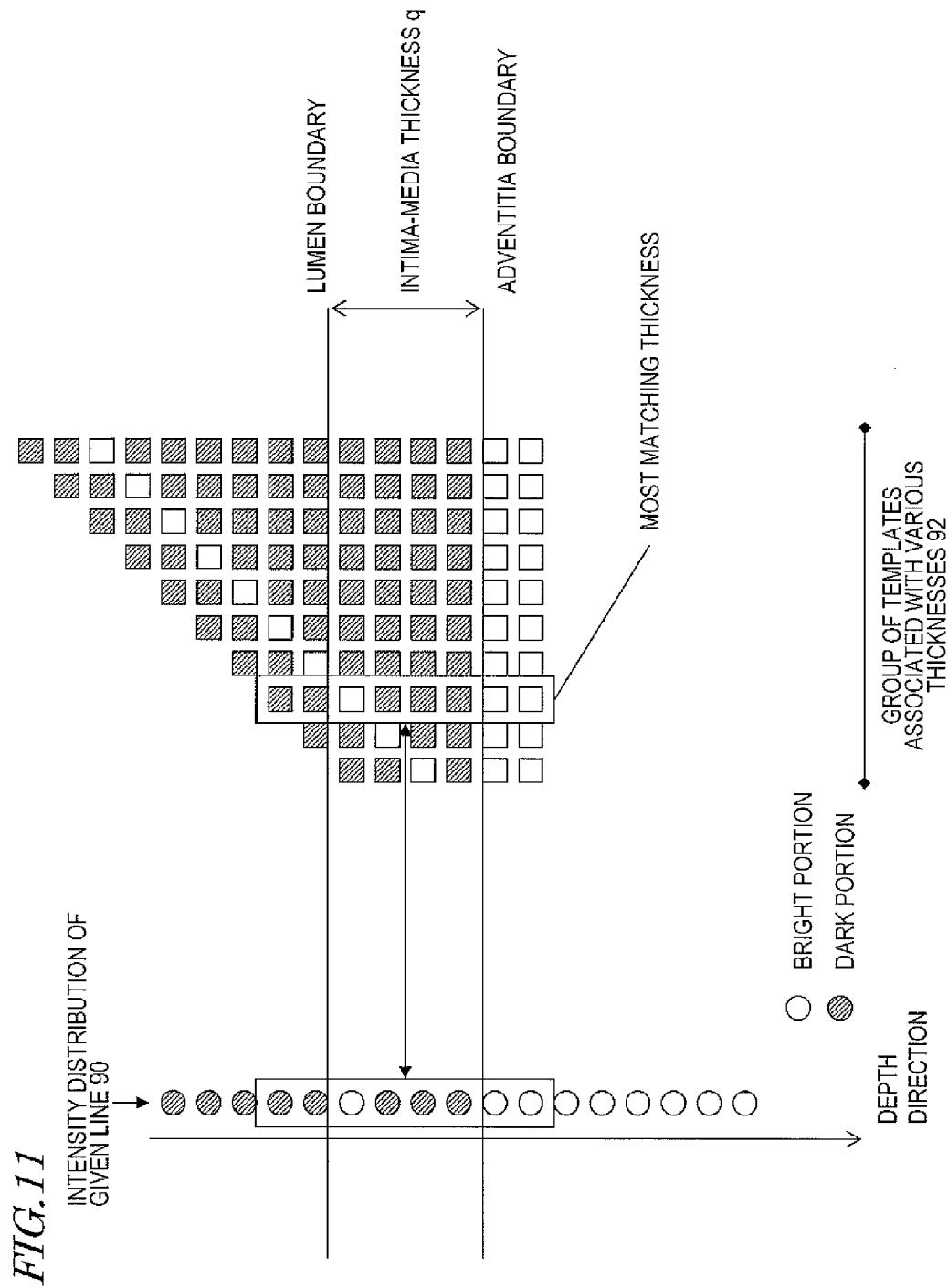

FIG. 11 illustrates the intensity distribution 90 of the given acoustic line (or line) and a group 92 of templates associated with various thicknesses.

Figure 12:
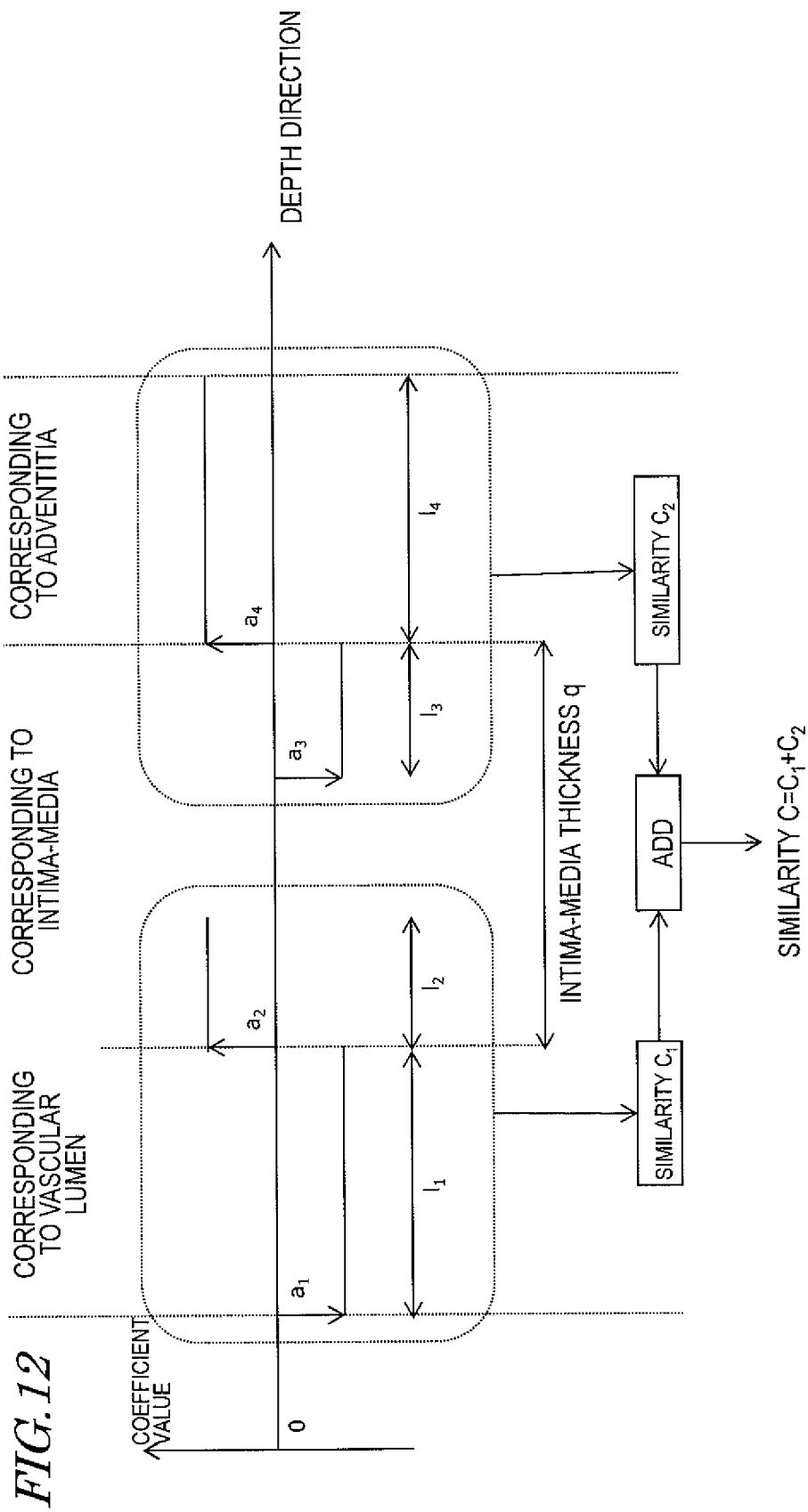

FIG. 12 shows an example in which the degree of similarity is calculated by providing sub-templates for the lumen and adventitia boundaries, respectively, calculating respective degrees of similarity using the sub-templates and then obtaining their combination value as a weighted sum.

Figure 13:
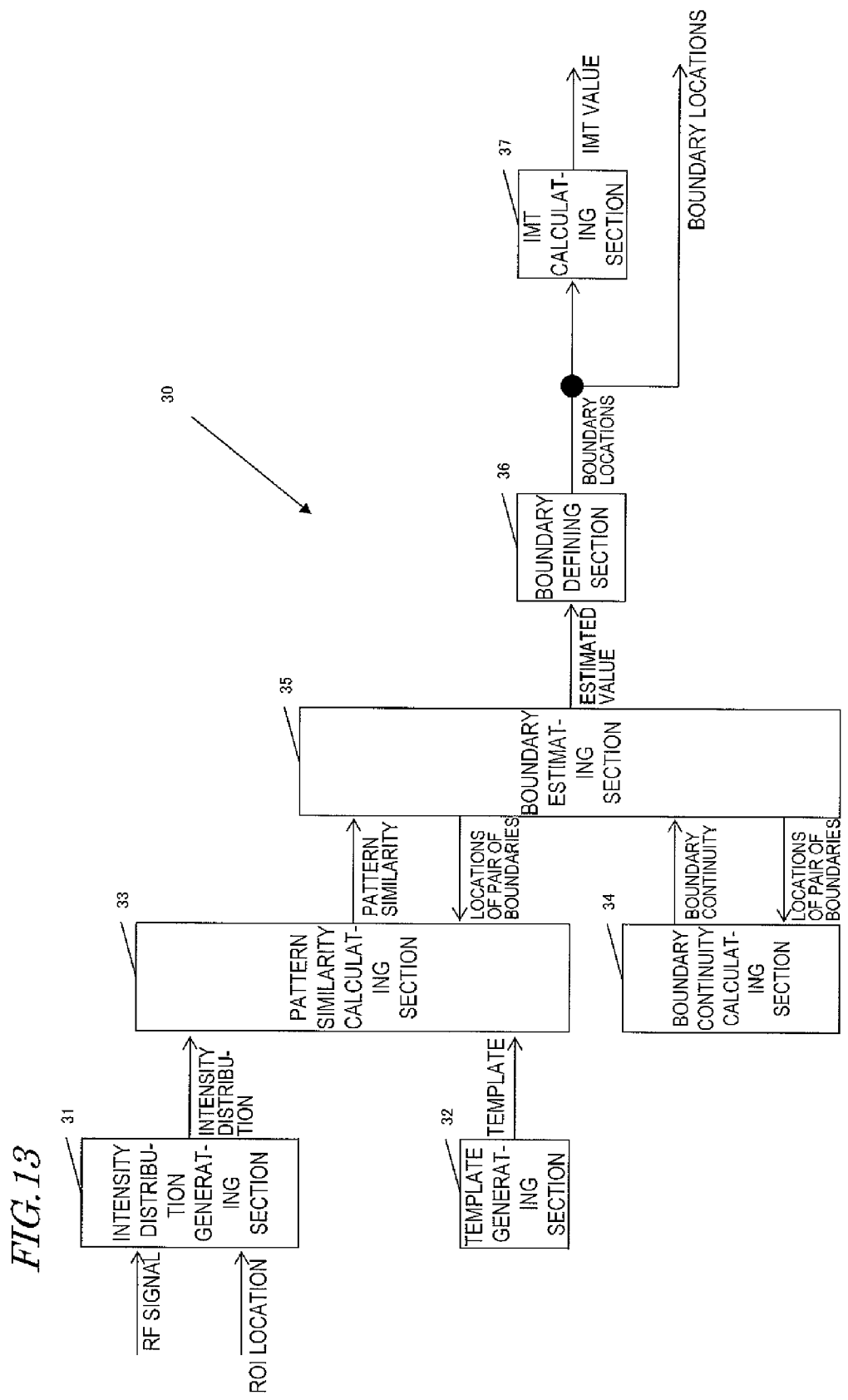

FIG. 13 is a block diagram illustrating a configuration for an IMT measuring section 30 according to a second specific preferred embodiment of the present invention.

FIG. 14 is a flowchart showing the procedure of the boundary detection processing based on dynamic programming.

Figure 15:
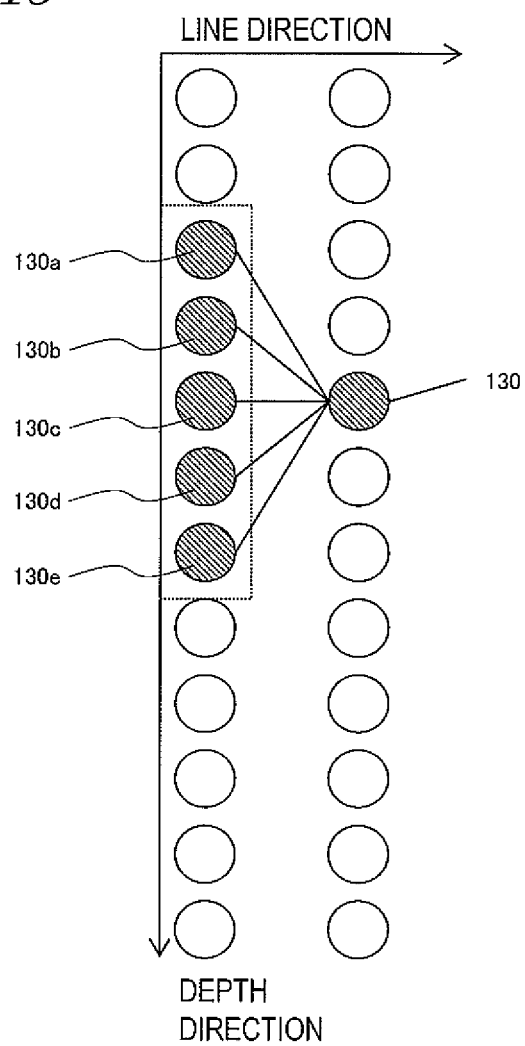

FIG. 15 illustrates five paths of interest 130a through 130e that have been determined in advance with respect to a single given sample 130.

Figure 16:
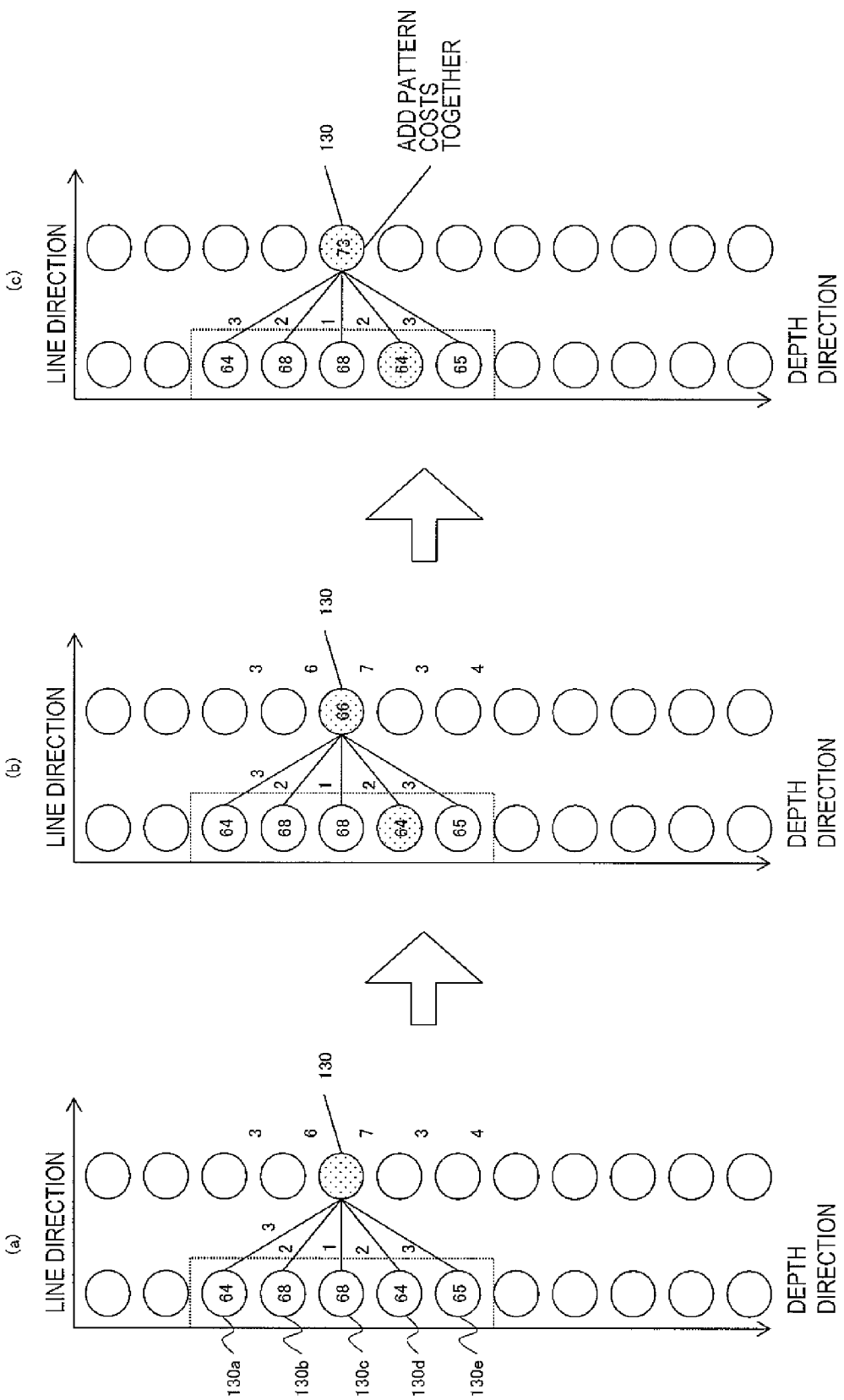

Portions (a) to (c) of FIG. 16 illustrate how to calculate the cost by dynamic programming according to the second preferred embodiment of the present invention.

Figure 17:
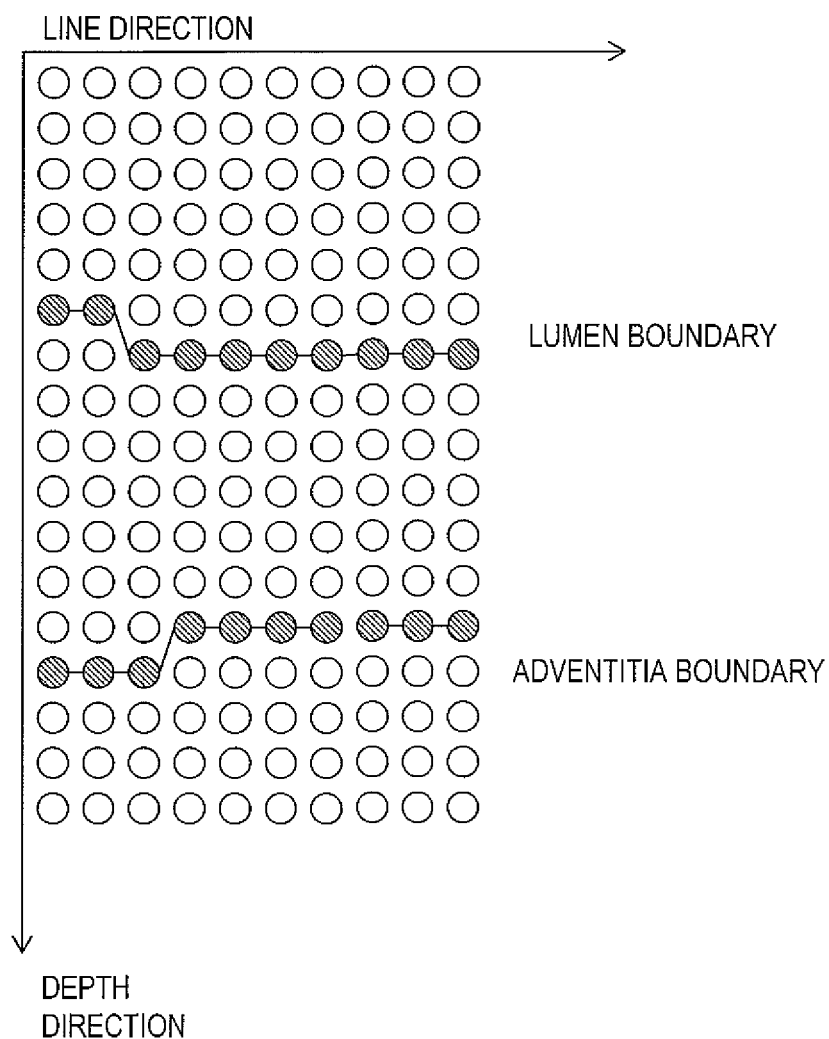

FIG. 17 illustrates an exemplary pair $i_{line}$ of lumen and adventitia boundaries that would minimize the path cost $C_{path}$.

Figure 18:
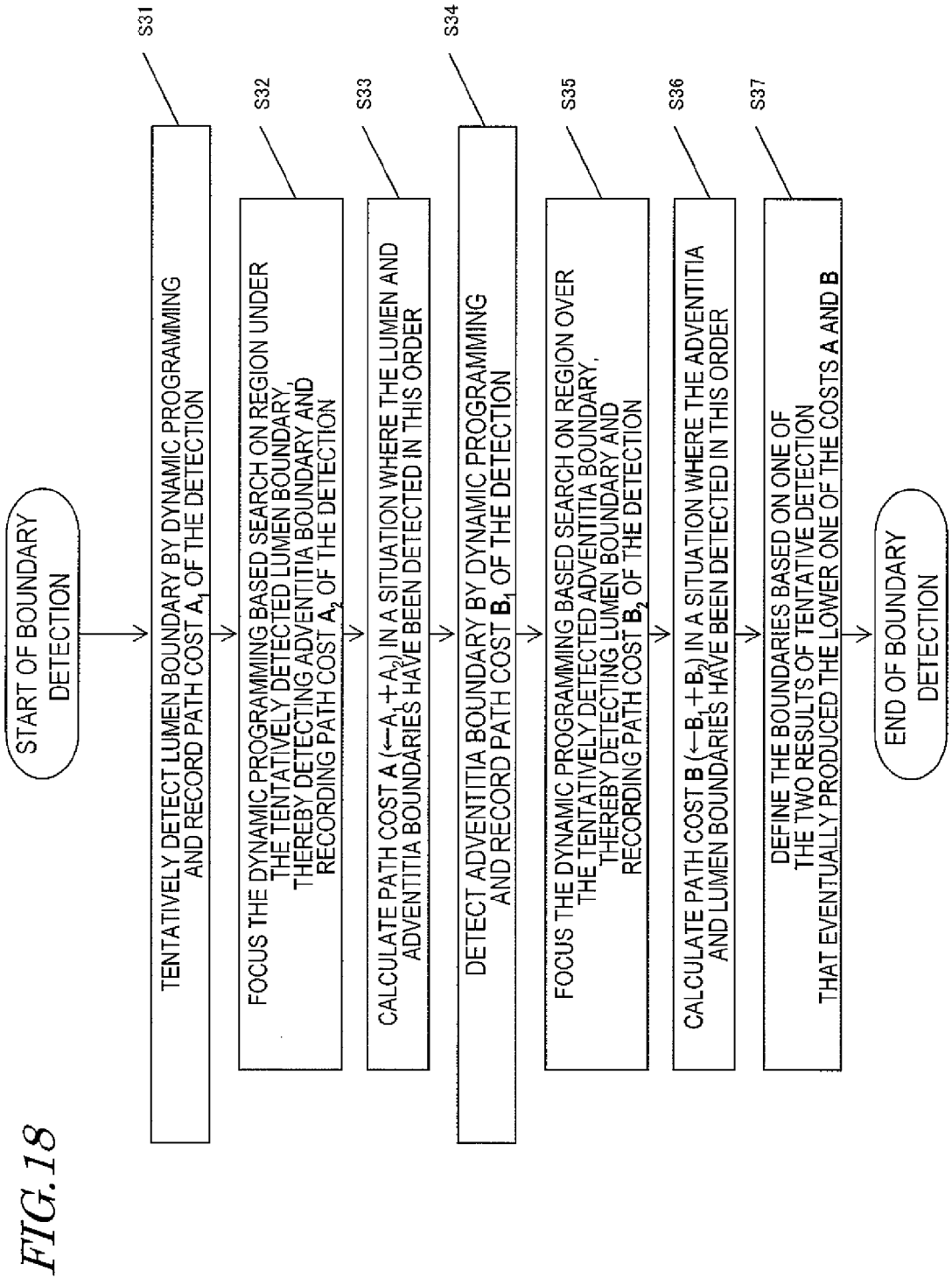

FIG. 18 is a flowchart showing the procedure of processing for making path searches for the lumen and adventitia boundaries separately from each other.

Figure 19:
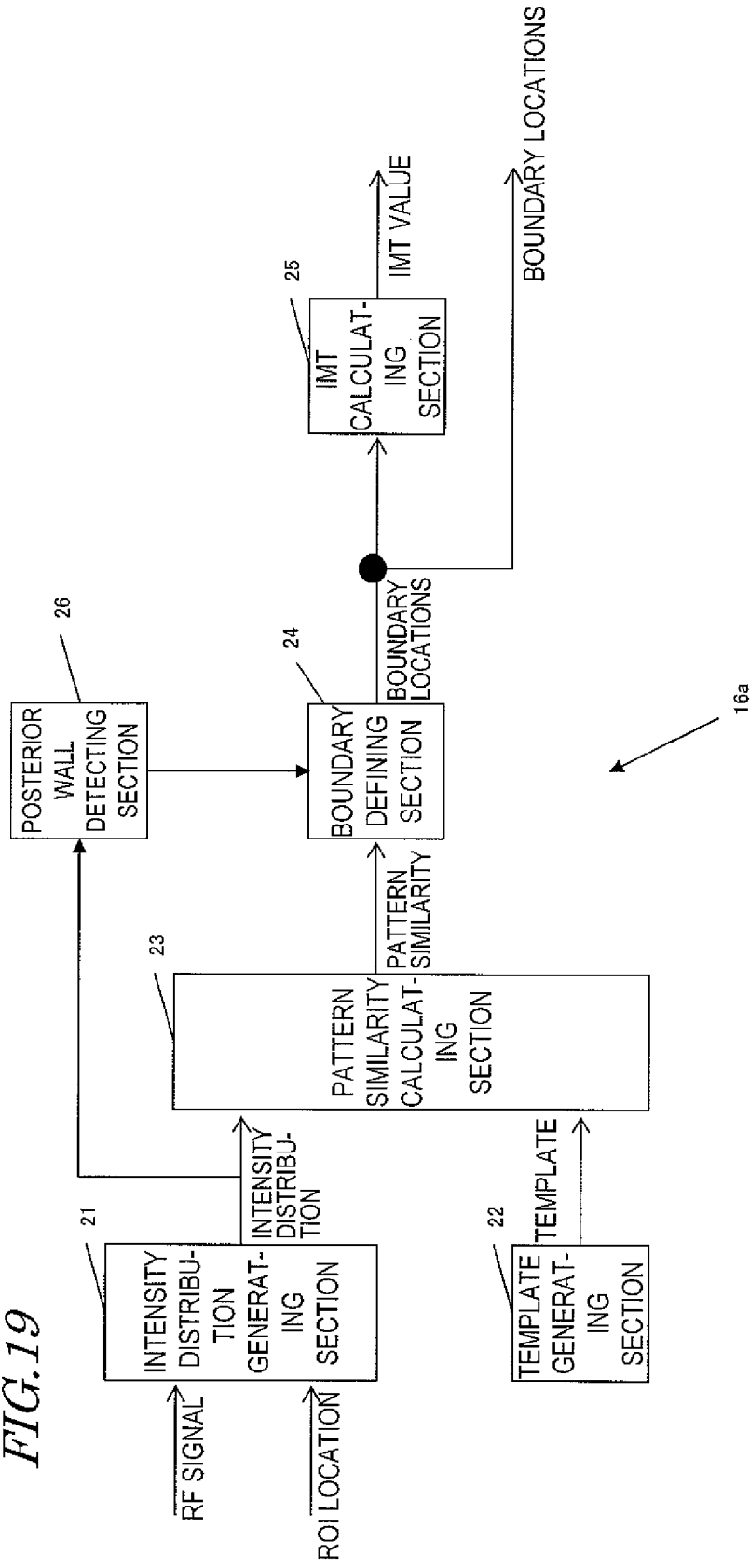

FIG. 19 is a block diagram illustrating a configuration for an IMT measuring section 16a with a posterior wall detecting section 26.

DESCRIPTION OF EMBODIMENTS

Hereinafter, preferred embodiments of an ultrasonic diagnostic apparatus according to the present invention will be described with reference to the accompanying drawings.

Embodiment 1

Figure 4:
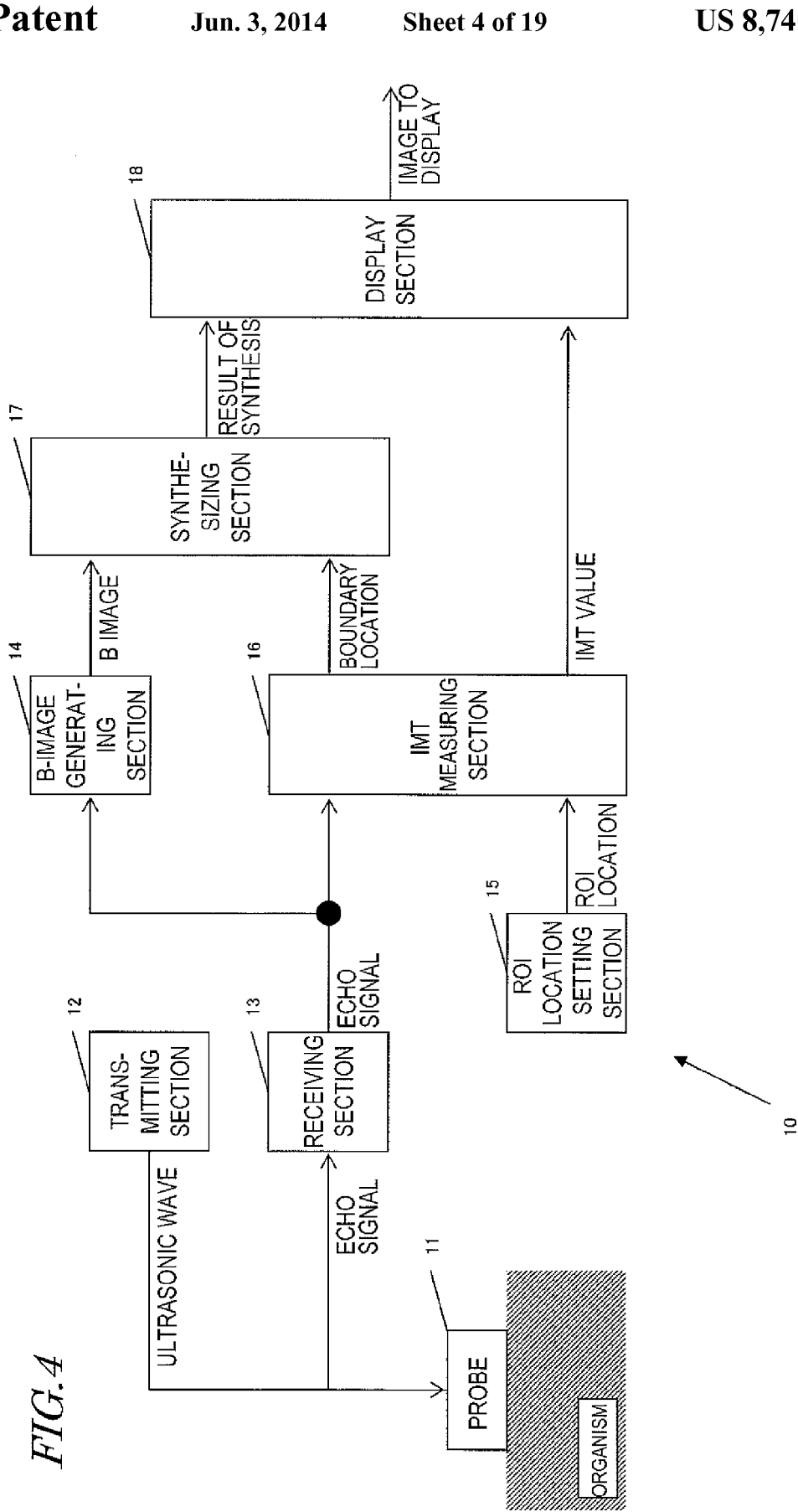
FIG. 4 is a block diagram illustrating a configuration for an ultrasonic diagnostic apparatus 10 as a first specific preferred embodiment of the present invention.

FIG. 4 is a block diagram illustrating a configuration for an ultrasonic diagnostic apparatus 10 as a first specific preferred embodiment of the present invention.

The ultrasonic diagnostic apparatus 10 includes a probe 11, a transmitting section 12, a receiving section 13, a B-image generating section 14, an ROI location setting section 15, an IMT measuring section 16, a synthesizing section 17 and a display section 18.

The transmitting section 12 generates an ultrasonic pulse and outputs it to the probe 11.

The probe 11 transmits the ultrasonic pulse, which has been supplied from the transmitting section 12, toward the inside of an organism and receives an echo signal that has been reflected back from inside of the organism. Then, the probe 11 outputs the echo signal received to the receiving section 13.

Figure 5:
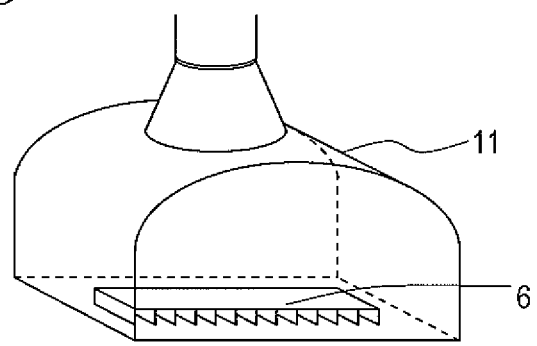
FIG. 5 illustrates an array 6 of ultrasonic transducers, which are built in an ultrasonic probe 11 in order to transmit an ultrasonic pulse.

FIG. 5 illustrates an array 6 of ultrasonic transducers, which are built in the ultrasonic probe 11 in order to transmit an ultrasonic pulse. In the array 6 of ultrasonic transducers (which will be simply referred to herein as "a transducer 6"), the respective ultrasonic transducers are arranged in one direction, thereby forming a so-called "1D array of transducers".

The transducer 6 may be made of a piezoelectric material, for example. That is to say, an ultrasonic wave is transmitted by driving the piezoelectric material, and is received and transformed into an electrical signal by the piezoelectric material. Also, by sequentially driving the respective ultrasonic transducers, the transducer 6 can transmit and receive ultrasonic waves and can scan a predetermined range with the ultrasonic waves. The transducer 6 can also superpose the phases of the respective ultrasonic waves that have been sent out from multiple ultrasonic transducers at a predetermined position (i.e., at a focus position) and can receive a signal that has been reflected from that focus position. An example of the latter operation is illustrated in FIG. 6.

Portions (a) and (b) of FIG. 6 illustrate ultrasonic converged waves in a situation where a focus position is formed by a number of ultrasonic transducers that are arranged in the x direction. As shown in FIG. 6, the ultrasonic converged wave has a predetermined width and has a focal point at a predetermined depth in the z-axis direction. The center axis of such a converged wave is also called an "acoustic line" as shown in portion (c) and (d) of FIG. 6.

Now take a look at FIG. 4 again. The receiving section 13 outputs a bunch of echo signals that have been supplied from the probe 11 to the B-image generating section 14 and the IMT measuring section 16.

The B-image generating section 14 generates a tomographic image based on the echo signals and provides the data of the tomographic image to the synthesizing section 17.

The ROI location setting section 15 accepts a user's instruction on where to set an ROI (region of interest) and sets it on an arterial wall in accordance with his or her instruction.

The IMT measuring section 16 measures the IMT. More specifically, based on the echo signal supplied from the receiving section 13 and information about the location of the ROI provided by the ROI location setting section 15, the IMT measuring section 16 detects a lumen boundary and an adventitia boundary. Furthermore, based on the locations of the lumen and adventitia boundaries detected, the IMT measuring section 16 calculates an IMT value. Then, the IMT measuring section 16 outputs information about the boundary locations (which will be referred to herein as "boundary location information") to the synthesizing section 17 and the IMT value to the display section 18, respectively.

The synthesizing section 17 receives the B-image data and the boundary location information from the B-image generating section 14 and the IMT measuring section 16, respectively, and synthesizes the IMT value and the B image together. Specifically, the synthesizing section 17 superimposes the images of the lumen and adventitia boundaries on the B image and outputs synthetic image data thus obtained.

The display section 18 displays, on a monitor, the IMT value and the synthetic image provided by the IMT measuring section 16 and the synthesizing section 17, respectively.

The display section 18 may display the synthetic image data, provided by the synthesizing section 17, on a display device such as an LCD.

Next, the IMT measuring section 16 will be described in detail.

FIG. 7 is a block diagram illustrating a configuration for the IMT measuring section 16.

The IMT measuring section 16 includes an intensity distribution generating section 21, a template generating section 22, a pattern similarity calculating section 23, a boundary defining section 24 and an IMT calculating section 25.

The intensity distribution generating section 21 generates an echo intensity distribution based on the echo signals supplied from the receiving section 13 and the information about the ROI location provided by the ROI location setting section 15, and then outputs the intensity distribution thus generated to the pattern similarity calculating section 23. This echo intensity distribution represents the distribution of intensities of the echo signals in the depth direction (i.e., as measured toward the depth of the body under its surface skin).

The template generating section 22 generates a template for use to detect a boundary based on another template that has been provided in advance to represent a reference pattern of the echo intensity distribution, and then outputs the template for detecting the boundary to the pattern similarity calculating section 23.

The pattern similarity calculating section 23 calculates the degree of similarity between the intensity distribution of the received signals supplied from the intensity distribution generating section 21 and the template given by the template generating section 22. The degree of similarity between them will be referred to herein as "pattern similarity". Then, the pattern similarity calculating section 23 outputs the degree of similarity calculated to the boundary defining section 24.

The boundary defining section 24 defines a lumen boundary and an adventitia boundary based on the pattern similarity provided by the pattern similarity calculating section 23. Then, the boundary defining section 24 provides information about the boundary location thus defined for the synthesizing section 18 and the IMT calculating section 25.

The IMT calculating section 25 calculates an IMT value based on the lumen and adventitia boundaries thus defined and outputs it to the display section 17.

Next, it will be described exactly how to calculate the IMT according to this preferred embodiment.

FIG. 8 is a flowchart showing the procedure of IMT calculation processing.

First of all, in Step S11, the intensity distribution generating section 21 carries out an envelope detection and a logarithmic compression on the echo signal received with respect to each point in the ROI, thereby generating an echo intensity distribution.

Next, in Step S12, the intensity distribution generating section 21 smoothes out the intensity distribution by applying a 3×3 average filter, for example, to the intensity distribution in order to reduce the noise.

After that, the pattern similarity calculating section 23 takes charge of the processing, which will be performed on the basis of an acoustic line (i.e., on a line-by-line basis).

First, in Step S13, the pattern similarity calculating section 23 estimates the degree of similarity between the intensity distribution in the ROI and a template representing the intima-media pattern. The template has been generated by the template generating section 22.

As the template, a coefficient pattern (intima-media pattern) such as the one shown in FIG. 9 is used. In FIG. 9, the range $l_1$ corresponds to the vascular lumen, the ranges $l_2$ and $l_3$ correspond to the intima-media, and the range $l_4$ corresponds to the adventitia. The template shown in FIG. 9 is a differential filter, in which the ranges $l_1$ and $l_3$ that have negative values in the depth direction and the ranges $l_2$ and $l_4$ that have positive values in the same direction are provided alternately in advance as reference coefficient patterns. As shown in FIG. 9, the template has at least three regions (or patterns) that correspond to the vascular lumen, the intima-media and the adventitia, respectively.

While moving this template as a detection window in the depth direction as shown in FIG. 10, the pattern similarity calculating section 23 estimates the degree of similarity and searches for the most matching depth.

In addition, the pattern similarity calculating section 23 also estimates the degree of similarity with respect to the intima-media thickness. That is to say, as shown in FIG. 11, the pattern similarity calculating section 23 gets a number of templates with various intima-media thicknesses generated by the template generating section 22, calculates the degree of similarity between those templates and the intensity distribution, and searches for the most matching thickness.

This processing step will be described in further detail.

FIG. 10 illustrates the intensity distribution 90 of a given acoustic line (which will be simply referred to herein as a "line") and a group 91 of templates that are associated with various depths. Each of those templates in the group 91 is a pattern that forms a single line in the depth direction parallel to the acoustic line. In FIG. 10, shown are ten templates that are associated with the depths p1, p2, p3, p4, . . . and p10, respectively. It should be noted that those templates are just associated with mutually different depths but have quite the same pattern.

First of all, the pattern similarity calculating section 23 calculates the degree of similarity between the intensity distribution 90 of the given acoustic line (or line) and the template that is associated with the depth p1 and an intima-media thickness q.

The degree of similarity is given as the inner product of the template T and the intensity distribution X. Supposing the intensity distribution at a depth p is identified by Xp, the intima-media thickness of the template is identified by q, the template associated with the intima-media thickness q is identified by Tq, and the size of that template is identified by L, the degree of similarity Y is calculated by the following equation:

$$Y(p, q) = \sum_{i=1}^{L} X_p(i) \cdot T_q(i)$$

In the example illustrated in FIG. 10, at the most matching depth p4, the patterns of the intima-media thickness q agree with each other between the template and the intensity distribution 90 of the given line. However, this is just an example to make the idea of the present invention easily understandable. Actually, even at the most matching depth, the intima-media thickness q patterns do not always agree with each other between the template and the intensity distribution 90 of the given line.

Thus, according to this preferred embodiment, the pattern similarity calculating section 23 calculates the degrees of similarity with the pattern of the intima-media thickness q changed at the depth p1. FIG. 11 illustrates the intensity distribution 90 of the given acoustic line (or line) and a group 92 of templates associated with various thicknesses. While varying the intima-media thickness q, the pattern similarity calculating section 23 calculates a degree of similarity Y with respect to each of those thicknesses.

Next, the pattern similarity calculating section 23 changes the depth into p2 and calculates the degree of similarity Y with the intima-media thickness q varied.

And such processing will be carried out continuity through the depth p10.

Then, the boundary defining section 24 searches for a depth p_max and an intima-media thickness q_max, which are associated with the highest degree of similarity Y (p, q), in Step S14 shown in FIG. 8 and then defines a lumen boundary li and an adventitia boundary ma in the next processing step S15. Specifically, if the length of the vascular lumen is identified by 11, those boundaries li and ma are calculated by the following equations:

$$li = p\_max + /1$$

$$ma + li + q\_max$$

The line-by-line processing is carried out in this manner.

In this processing, to prevent the degrees of similarity from being concentrated on a particular intima-media thickness, coefficient values $a_1'$, $a_2'$, $a_3'$ and $a_4'$ may be set to be the inverse numbers of their associated range lengths $l_1$, $l_2$, $l_3$ and $l_4$. That is to say, the average of the intensities of the respective regions that are associated with the range lengths $l_1$, $l_2$, $l_3$ and $l_4$ is calculated and then weighted. In that case, the degree of similarity is calculated by the following equation:

$$Y(p,q) = -\frac{a_1'}{l_1} \cdot \sum_{i=1}^{l_1} X_p(i) + \frac{a_2'}{l_2} \cdot \sum_{i=l_1+1}^{l_1+l_2} X_p(i) -$$

-continued $$\frac{a_3'}{l_3} \cdot \sum_{i=l_1+l_2+1}^{l_1+l_2+l_3} X_p(i) + \frac{a_4'}{l_4} \cdot \sum_{i=l_1+l_2+l_3+1}^{l_1+l_2+l_3+l_4} X_p(i)$$

where $a_1'$, $a_2'$, $a_3'$ and $a_4'$ are weight coefficients.

If the intima-media thickness needs to be further varied, $l_3$ may be changed with $l_2$ fixed or both $l_2$ and $l_3$ may be changed at a predetermined ratio.

Next, in Step S15, the lines are changed into the next one. The same series of processing steps described above will be performed on each of those lines.

And when the line-by-line processing gets done, the boundary locations are smoothed out in Step S16 in the line direction.

This is the flow of the operation of this first preferred embodiment.

In the foregoing description, the degree of similarity is supposed to be obtained as the inner product of the intensity distribution and a template that is implemented as a differential filter. However, the degree of similarity may also be obtained as their correlation. In that case, the coefficient values of the template do not have to include negative values.

Also, the degree of similarity may also be calculated by providing sub-templates for the lumen and adventitia boundaries, respectively, as shown in FIG. 12, calculating respective degrees of similarity using the sub-templates and then obtaining their combination value as a weighted sum, for example. Each of those sub-templates defines a pattern representing its associated boundary and a pattern representing the other tissue. However, these patterns are changeable. That is to say, the location of the pattern representing the boundary can be changed. In each of these two templates, the boundary region and a region corresponding to the other tissue represent a high-echo tissue region and a low-echo tissue region, respectively.

Furthermore, the coefficient values of each template may also be changed according to the degree of visualization in the ROI. For example, if the variance of the intensity values calculated turns out to be large, the contrast of the template may be enhanced. On the other hand, if the variance turns out to be small, then the contrast may be lessened.

Furthermore, in the foregoing description, the lumen and adventitia boundaries are supposed to be detected directly. Instead, the posterior wall may be detected first using a differential filter, and then the lumen and adventitia boundaries may be detected only inside of the posterior wall. This should work effectively if multiple echoes are produced inside of the blood vessel.

According to the first preferred embodiment of the present invention described above, the lumen and adventitia boundaries are located by finding what template has the highest degree of similarity to the intensity distribution of a given line. The template defines the pattern of the intensity distribution that covers the lumen and adventitia boundaries. This means that the lumen and adventitia boundaries are detected with their respective intensity variations taken into account, instead of detecting the lumen and adventitia boundaries independently of each other. Consequently, even if the intensity of the lumen boundary is greater than that of the adventitia boundary, the lumen boundary will never be taken for the adventitia boundary by mistake.

Embodiment 2

In a second specific preferred embodiment of the present invention, the IMT measuring section performs its processing differently from its counterpart of the first preferred embodiment described above. Specifically, before smoothing out the boundaries in the line direction, the IMT measuring section of this preferred embodiment selects the boundaries with not only the pattern similarity but also the continuity in the line direction taken into account. By carrying out such processing, the boundaries can be detected with good stability even if the lumen boundary cannot be located definitely based on only its associated intensity.

The configuration and operation of the ultrasonic diagnostic apparatus of this preferred embodiment are the same as those of the ultrasonic diagnostic apparatus 10 shown in FIG. 4 except its IMT measuring section. Thus, FIG. 4 will also be referred to when the configuration of the ultrasonic diagnostic apparatus of this preferred embodiment is described and description of every element of the apparatus other than its IMT measuring section will be omitted herein.

FIG. 13 is a block diagram illustrating a configuration for the IMT measuring section 30 of this preferred embodiment.

The IMT measuring section 30 includes an intensity distribution generating section 31, a template generating section 32, a pattern similarity calculating section 33, a boundary continuity calculating section 34, a boundary estimating section 35, a boundary defining section 36 and an IMT calculating section 37.

The intensity distribution generating section 31 generates an echo intensity distribution based on the echo signals supplied from the receiving section 13 and the information about the ROI location provided by the ROI location setting section 15, and then outputs the intensity distribution thus generated to the pattern similarity calculating section 23.

The template generating section 32 generates a template for use to detect a boundary based on another template that has been provided in advance to represent a reference pattern, and then outputs the template for detecting the boundary to the pattern similarity calculating section 33.

The pattern similarity calculating section 33 receives the intensity distribution of the received signals from the intensity distribution generating section 31 and the template from the template generating section 22, respectively, and also receives instructions on the locations of the lumen and adventitia boundaries from the boundary estimating section 35. More specifically, with respect to the respective locations of the lumen and adventitia boundaries that are specified by the boundary estimating section 35, the pattern similarity calculating section 33 calculates the degrees of similarity between the intensity distributions of the received signals at those locations and the template provided by the template generating section 22. Then, the pattern similarity calculating section 33 outputs the degrees of similarity calculated to the boundary estimating section 35.

The boundary continuity calculating section 34 receives the instructions on the locations of the lumen and adventitia boundaries from the boundary estimating section 35. With respect to those specified locations of the lumen and adventitia boundaries, the boundary continuity calculating section 34 estimates the degrees of continuity between the boundary locations in the line direction and the thickness using the given line and its adjacent lines. Then, the boundary continuity calculating section 34 outputs the result of the estimation as the "degree of continuity" to the boundary estimating section 35.

Based on the degree of pattern similarity supplied from the pattern similarity calculating section 33 and the degree of boundary continuity supplied from the boundary continuity calculating section 34, the boundary estimating section 35 estimates the likelihood values of lumen and adventitia boundaries with respect to every predefined combination of boundaries. Those estimated values are calculated by dynamic programming as will be described later. Then, the boundary estimating section 35 outputs the estimated values thus calculated to the boundary defining section 36.

The boundary defining section 36 defines a lumen boundary and an adventitia boundary based on the estimated values provided by the boundary estimating section 34. Then, the boundary defining section 36 provides information about the boundary location thus defined for the synthesizing section 18 and the IMT calculating section 37.

The IMT calculating section 37 calculates an IMT value based on the lumen and adventitia boundaries thus defined and outputs it to the display section 17. This processing is the same as what is performed by the IMT calculating section 25 shown in FIG. 7.

Next, it will be described exactly how to detect the boundaries according to this preferred embodiment. The boundary detection processing to be described below is performed mainly by the boundary continuity calculating section 34, the boundary estimating section 35 and the boundary defining section 36.

FIG. 14 is a flowchart showing the procedure of the boundary detection processing based on dynamic programming.

According to this preferred embodiment, the boundary detection processing is carried out as a search for a path (i.e., a boundary) in the line direction that would minimize the cost that is defined by the pattern similarity and the boundary continuity in the line direction.

First of all, in Step S21, the boundary estimating section 35 initializes the path cost $C_{path}$ of every pair $i_{line}$ of lumen and adventitia boundaries. The initial value is given as the degree of similarity $C_{pattern}$ to the intima-media pattern. Supposing the weight is identified by $W_{pattern}$, the path cost $C_{path}$ is given by the following formula:

$$C_{path}(i_{line}) \leftarrow -W_{pattern} \cdot C_{pattern}(i_{line})$$

In this case, the degree of similarity $C_{pattern}$ is a value similar to what has already been described for the first preferred embodiment. It should be noted, however, that the degree of similarity has been normalized within the line. Nevertheless, the degree of similarity does not have to be normalized within the entire line. For example, values within only a portion of the line associated with at least the intima-media may be normalized.

Also, the "pair of lumen and adventitia boundaries" is equivalent to a combination of lumen and adventitia boundaries. If there are N sample points on the ROI, the number of pairs is the square of N. Nonetheless, the lumen boundary is located at a shallower level than the adventitia boundary. Or depending on a constraint imposed by the system (such as the maximum thickness measured), the number of pairs actually used to make a calculation is smaller than the square of N.

Next, the targets of processing are changed into the second line.

Then, in Step S22, the pattern similarity calculating section 33 calculates the degree of similarity of the intima-media pattern to each pair $i_{line-1}$ of lumen and adventitia boundaries of the previous line. Meanwhile, the boundary continuity calculating section 34 calculates the degree of continuity between the intima-media thickness and the boundary locations with respect to each pair $i_{line-1}$ of lumen and adventitia boundaries of the previous line. Then, the boundary estimating section 35 receives the results of those calculations and estimates the degree of continuity between the intima-media thickness and the boundary locations in the line direction.

In this case, the degree of similarity $C_{pattern}$ of the intima-media pattern is given as the inner product of the intensity distribution and the template as in the first preferred embodiment described above but may also be given as their correlation.

If the lumen boundary locations of a given line and its previous line are identified by $LI_{line}$ and $IL_{line-1}$ and the adventitia boundary locations thereof are identified by $MA_{line}$ and $MA_{line-1}$, respectively, then the degree of continuity $C_{Thickness}$ of the intima-media thickness is calculated by the following equation:

$$C_{thickness}(i_{line-1}) = |(MA_{line} - LI_{line}) - (MA_{line-1})|$$

Meanwhile, the degree of continuity $C_{distance}$ of the boundary locations is calculated by the following equation:

$$C_{distance}(i_{line-1}) = |LI_{line} - LI_{line-1}| + |MA_{line} - MA_{line-1}|$$

The boundary estimating section 35 normalizes the estimated values $C_{Thickness}$ and $C_{distance}$ within the line and then integrates them into the path cost $C_{total}$ of the candidate to adopt as in the following equation:

$$C_{total}(i_{line-1}) = C_{path}(i_{line-1}) + W_{thickness} \cdot C_{thickness}(i_{line-1}) + W_{distance} \cdot C_{distance}(i_{line-1})$$

where the weights $W_{thickness}$ and $W_{distance}$ are weight coefficients to be added to each estimated value. Even though this equation includes the estimated values $C_{Thickness}$ and $C_{distance}$, just the degree of continuity $C_{distance}$ of the boundary locations has to be included and the degree of continuity $C_{Thickness}$ of the intima-media thickness could be omitted.

The boundary estimating section 35 carries out these calculations on each of multiple pairs $i_{line-1}$ of lumen and adventitia boundaries associated with predetermined paths of interest.

For example, in FIG. 15, five predetermined paths of interest 130a through 130e are shown with respect to a single given sample 130 (e.g., a candidate to adopt as the lumen boundary). The boundary estimating section 35 calculates the cost as described above with respect to the path that is determined as the combination of the given sample 130 and each of the paths of interest 130a through 130e.

Portions (a) to (a) of FIG. 16 illustrate how to calculate the cost by dynamic programming according to this preferred embodiment. In portion (a) of FIG. 16, the numerical values shown inside of the respective paths of interest 130a through 130e indicate the accumulated values of the path costs. On the other hand, the numerical values shown beside the line segments that connect together the given sample 130 and the respective paths of interest 130a through 130e indicate distance costs. And the numerical values shown on the right-hand side of the given sample 130 in the depth direction indicate pattern costs.

As shown in portion (b) of FIG. 16, the boundary estimating section 35 adopts one of the five paths of interest 130a through 130e, of which the sum of the accumulated path cost and the distance cost is smaller than any other path of interest. In the example illustrated in portion (b) of FIG. 16, the path 130d with a sum of 66 is adopted. Then, the boundary estimating section 35 memorizes that path that would have the minimum cost.

And the boundary estimating section 35 further adds the pattern cost to the minimum value described above and defines the sum as the value of the given sample 130.

Now take a look at FIG. 14 again. In Step S23, the minimum cost $C_{total}$ and its associated pair of lumen and adventitia boundaries are searched for and adopted as the path. In this processing step, the path adopted is memorized and the path cost is updated by the following equation:

$$C_{path}(i_{line}) \leftarrow -W_{pattern} \cdot C_{pattern}(i_{line}) + \min_{i_{line-1}}[C_{total}(i_{line-1})]$$

These processing steps S22 and S23 are carried out on every pair $i_{line}$ of lumen and adventitia boundaries on the target line. Then, the boundary estimating section 35 sends the results thus obtained to the boundary defining section 36.

After the calculations are done on every line, the boundary defining section 36 searches in Step S26 for a pair $i_{line}$ of lumen and adventitia boundaries that would minimize the path cost $C_{path}$. In this case, the pair that would minimize the path cost $C_{path}$ will define the boundaries on the rightmost line of the ROI. After that, the other lines on the left-hand side of that rightmost line will be set by reference to the path memorized.

FIG. 17 illustrates an exemplary pair $i_{line}$ of lumen and adventitia boundaries that would minimize the path cost $C_{path}$.

This is the flow of processing of this preferred embodiment.

Optionally, the boundaries may be smoothed out in the line direction as in the first preferred embodiment described above. Then, smoother boundaries can be obtained.

Alternatively, such dynamic programming based path search may also be carried out on an intensity distribution, of which the resolution has been decreased (particularly in the depth direction) on purpose, to tentatively choose candidates. After that, the resolution may be restored to the original value, a narrower search may be carried out on only a region surrounding (i.e., in the vicinity of) the tentatively chosen candidates, and then the lumen and adventitia boundaries may be defined finally. In that case, the complexity of the processing can be cut down with the detection performance maintained.

Still alternatively, such dynamic programming based path search may also be focused on only some pairs that would have either smallest path costs or path costs that are equal to or smaller than a predetermined value. In that case, the complexity of the processing can be also cut down with the detection performance maintained.

Last but not least, although the path search is supposed to be carried out on a pair of lumen and adventitia boundaries, the path search could also be performed separately on the lumen and adventitia boundaries.

FIG. 18 is a flowchart showing the procedure of processing for making path searches for the lumen and adventitia boundaries separately from each other. According to this processing, the lumen boundary is detected first, and then the adventitia boundary is detected by narrowing the search on deeper levels. After that, the processing is carried out in reverse order. That is to say, the adventitia boundary is detected first, and then the lumen boundary is detected by narrowing the search on shallower levels. And one of these two pairs detected that would eventually have the smaller total path cost than the other is chosen.

Specifically, in Step S31, the boundary estimating section 35 tentatively detects the lumen boundary by dynamic programming and records its path cost $A_1$ based on the result of the detection. Next, in Step S32, the boundary estimating section 35 focuses the dynamic programming based search on a region under the tentatively detected lumen boundary, thereby detecting tentatively the adventitia boundary and recording its path cost $A_2$ based on the result of the detection.

Then, in Step S33, the boundary estimating section 35 calculates and records the path cost A (=$A_1+A_2$) in such a situation where the lumen and adventitia boundaries have been detected in this order.

Next, in Step S34, the boundary estimating section 35 tentatively detects the adventitia boundary by dynamic programming and records its path cost $B_1$ based on the result of the detection. Next, in Step S35, the boundary estimating section 35 focuses the dynamic programming based search on a region over the tentatively detected adventitia boundary, thereby detecting tentatively the lumen boundary and recording its path cost $B_2$ based on the result of the detection. Then, in Step S33, the boundary estimating section 35 calculates and records the path cost B (=$B_1+B_2$) in such a situation where the adventitia and lumen boundaries have been detected in this order.

And the boundary defining section 36 defines the adventitia and lumen boundaries based on one of these two results of tentative detection that eventually produced the lower one of the two costs A and B.

Nevertheless, when one of the two boundaries is detected, the other boundary has not been determined yet. That is why the degrees of close matching of multiple templates associated with various intima-media thicknesses may be estimated with one of two boundaries fixed and the other tentatively detected boundary moved, and either the maximum or average of the estimated values may be used as the degree of similarity as shown in FIG. 11. In this manner, the complexity of processing can also be cut down with the detection performance maintained.

As described above, since the boundary continuity in the line direction is taken into account according to this second preferred embodiment, the boundaries can be detected with good stability, even if the intensity of the echo signal that would represent the lumen boundary is low.

Figure 1:
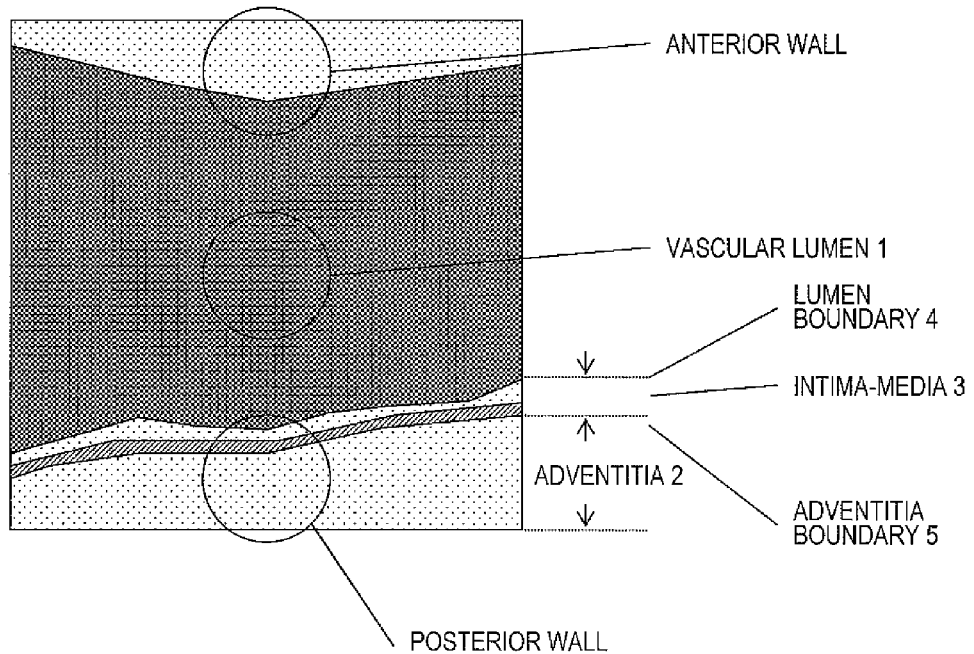
FIG. 1 illustrates an intima-media 3 that is present between the lumen 1 and adventitia 2 of a blood vessel.
Figure 2:
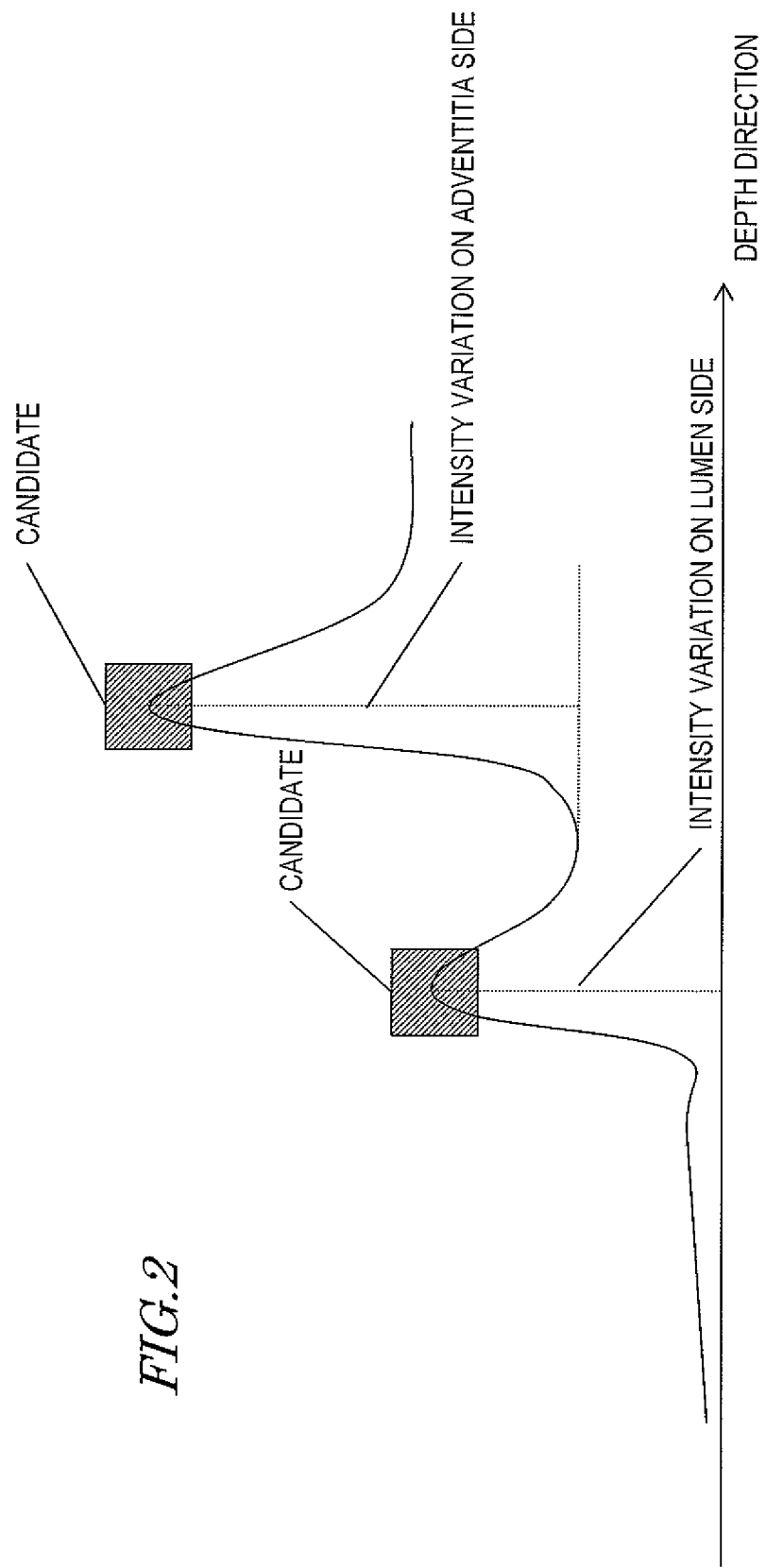
FIG. 2 shows the intensity distribution of an echo for use to define an adventitia boundary and a lumen boundary according to the technique disclosed in Patent Document No. 1.
Figure 3:
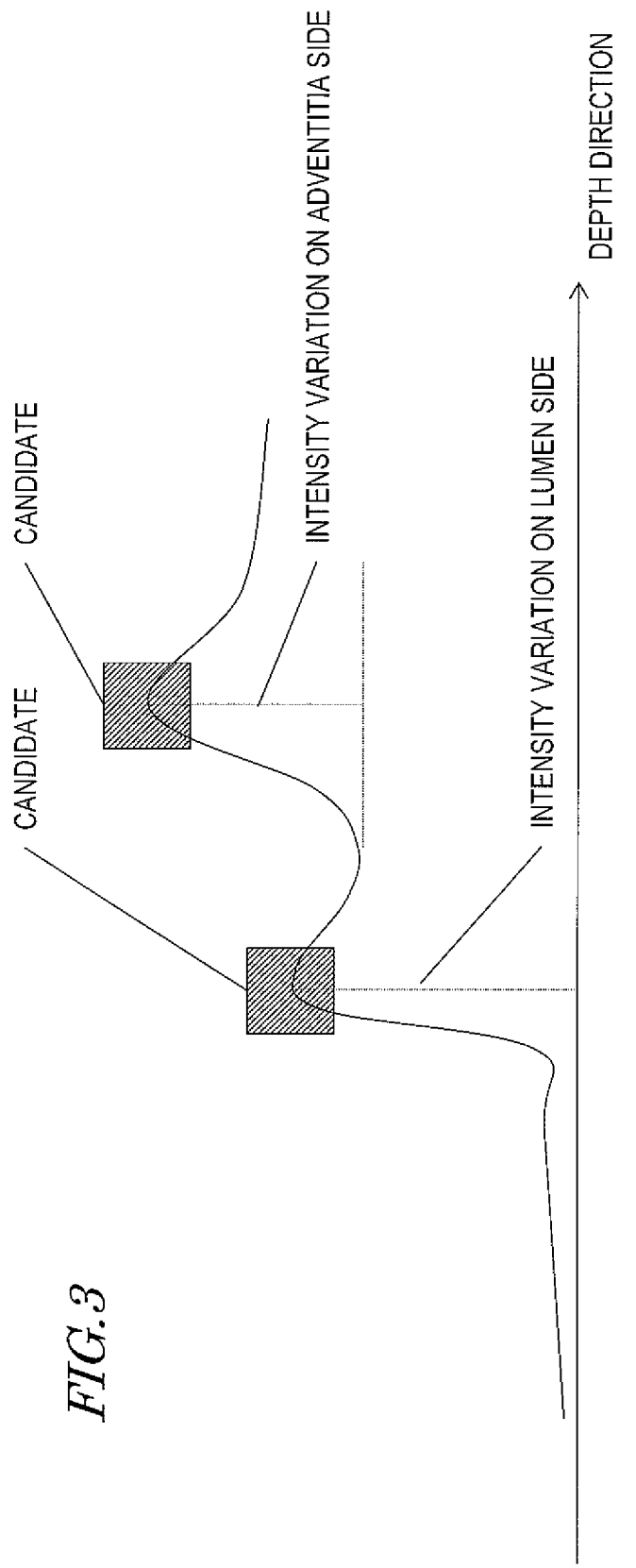
FIG. 3 illustrates an example in which the intensity variation of the lumen boundary is greater than that of the adventitia boundary.

Optionally, in the first and second preferred embodiments of the present invention described above, the posterior wall may be further detected and the result of detection may be used to define the boundaries. As shown in FIG. 1, the posterior wall is a region that is located at a deeper level than the adventitia boundary 5.

FIG. 19 is a block diagram illustrating a configuration for an IMT measuring section 16a with a posterior wall detecting section 26. In this case, the IMT measuring section 16a is a modified example of the IMT measuring section 16 of the first preferred embodiment shown in FIG. 7.

The posterior wall detecting section 26 is arranged to follow the intensity distribution generating section 21 and detects the posterior wall based on the intensity distribution provided by the intensity distribution generating section 21 and outputs the range of the posterior wall detected to the boundary defining section 24.

More specifically, as shown in FIG. 1, the posterior wall is a vascular wall and is located at a deeper level than the lumen boundary 4, the intima-media 3 or the adventitia boundary 5 in the depth direction. And the posterior wall is obtained as a high-echo region. That is why the posterior wall detecting section 26 detects a high-echo region based on the intensity distribution generated by the intensity distribution generating section 21. As a result, the boundary defining section 26 can define the adventitia boundary 5 with its search focused on the posterior wall range detected.

INDUSTRIAL APPLICABILITY

The IMT measuring apparatus of the present invention can measure the IMT accurately and automatically, and can contribute to getting the inspection done more quickly. Consequently, the apparatus of the present invention can be used effectively to make an arterial sclerosis screening inspection, in particular.

REFERENCE SIGNS LIST 11 probe
12 transmitting section
13 receiving section
14 B-image generating section
15 ROI location setting section
16 IMT measuring section
17 synthesizing section
18 display section
21 intensity distribution generating section
22 template generating section
23 pattern similarity calculating section
24 boundary defining section
25 IMT calculating section
26 posterior wall detecting section
27 contrast calculating section
28 detection window
31 intensity distribution generating section
32 template generating section
33 pattern similarity calculating section
34 boundary continuity calculating section
35 boundary estimating section
36 boundary defining section
37 IMT calculating section

The invention claimed is:

1. An ultrasonic diagnostic apparatus that transmits an ultrasonic wave toward a body and obtains biological information based on an echo signal that has been received from the body, the apparatus comprising:
   an intensity distribution generating section configured to generate an echo intensity distribution in a depth direction with respect to a vascular wall based on the echo signal;
   a template generating section configured to generate a template for use to detect a boundary based on template data that has been provided in advance to represent a reference pattern of the echo intensity distribution;
   a pattern similarity calculating section configured to change, in combination, the level of the template in the depth direction and a pattern of the template representing an intima-media thickness to calculate the degree of similarity between the template and the intensity distribution on any change made in the level or pattern of the template; and
   a boundary defining section configured to define a lumen boundary and an adventitia boundary based on the degree of similarity that has been calculated on any change made in the level or pattern of the template.

2. The ultrasonic diagnostic apparatus of claim 1, wherein the template generated by the template generating section includes at least three regions, one or more of which is a variable-length region with a variable range length.

3. The ultrasonic diagnostic apparatus of claim 2, wherein the at least three regions are arranged in order, and
   wherein the variable-length region is the middle one of the at least three regions.

4. The ultrasonic diagnostic apparatus of claim 3, wherein the variable-length region corresponds to an intima-media region of a blood vessel.

5. The ultrasonic diagnostic apparatus of claim 2, wherein one of the at least three regions that is located at one end corresponds to a low-echo tissue region and another one of the at least three regions that is located at the other end corresponds to a high-echo tissue region.

6. The ultrasonic diagnostic apparatus of claim 5, wherein the low-echo tissue region corresponds to a blood flow region and the high-echo tissue region corresponds to the adventitia wall of a blood vessel and a body tissue.

7. The ultrasonic diagnostic apparatus of claim 2, wherein the pattern similarity calculating section calculates the degree of similarity by normalizing the length of the variable-length region.

8. The ultrasonic diagnostic apparatus of claim 7, wherein the pattern similarity calculating section normalizes the length of the variable-length region by using the average intensity of the variable-length region as its intensity.

9. The ultrasonic diagnostic apparatus of claim 1, wherein the template generated by the template generating section is made up of two kinds of sub-templates, each of which is formed of at least two regions, the two kinds of sub-templates having a variable distance between themselves, and wherein the pattern similarity calculating section calculates two degrees of similarity using the two kinds of sub-templates and then combines and integrates the two degrees of similarity together to obtain the degree of similarity.

10. The ultrasonic diagnostic apparatus of claim 9, wherein the two regions that form each of the two kinds of sub-templates correspond to a low-echo tissue region and a high-echo tissue region, respectively.

11. The ultrasonic diagnostic apparatus of claim 9, wherein low- and high-echo tissue regions of the two kinds of sub-templates respectively correspond to either a blood flow region and an intima-media region or a lumen boundary and a predetermined tissue region that includes an adventitia boundary, an arterial adventitia wall and a body tissue.

12. The ultrasonic diagnostic apparatus of claim 1, wherein the template generating section changes a coefficient value of the template to generate according to the contrast of the intensity distribution that has been generated by the intensity distribution generating section.

13. The ultrasonic diagnostic apparatus of claim 1, wherein the degree of similarity estimated by the pattern similarity calculating section is defined by an intensity difference between boundaries as specified by the template that has been generated by the template generating section.

14. The ultrasonic diagnostic apparatus of claim 1, wherein the degree of similarity estimated by the pattern similarity calculating section is defined by a normalized correlation between the template that has been generated by the template generating section and the intensity distribution that has been generated by the intensity distribution generating section.

15. The ultrasonic diagnostic apparatus of claim 1, further comprising a posterior wall detecting section configured to detect a posterior wall region based on the intensity distribution that has been generated by the intensity distribution generating section, wherein the boundary defining section sets the boundaries only within the posterior wall range detected.

16. The ultrasonic diagnostic apparatus of claim 15, wherein the posterior wall region detected by the posterior wall detecting section corresponds to a vascular wall.

17. The ultrasonic diagnostic apparatus of claim 1, further comprising an IMT calculating section configured to calculate the thickness of an intima-media based on the levels of the lumen and adventitia boundaries.

18. An ultrasonic diagnostic apparatus that transmits an ultrasonic wave toward a body and obtains biological information based on an echo signal that has been received from the body, the apparatus comprising:

an intensity distribution generating section configured to generate an echo intensity distribution in a depth direction with respect to a vascular wall based on the echo signal;

a template generating section configured to generate a template for use to detect a boundary based on template data that has been provided in advance to represent a reference pattern of the echo intensity distribution;

a pattern similarity calculating section configured to change, in combination, a pattern of the template representing an intima-media thickness with respect to each of multiple different combinations of candidate boundaries that are located at mutually different levels in the depth direction to calculate the degree of similarity between the template and the intensity distribution on any change made in the pattern of the template;

a boundary continuity calculating section configured to calculate, with respect to the combination selected in association with multiple adjacent acoustic lines, the degree of continuity between the boundaries based on the degree of continuity of the locations of boundaries between the adjacent acoustic lines;

a boundary estimating section configured to generate an estimated value by integrating together the pattern similarity and the boundary continuity with respect to the combination; and a boundary defining section configured to define a lumen boundary and an adventitia boundary based on the integrated estimated value.

19. The ultrasonic diagnostic apparatus of claim 1, wherein the boundary estimating section calculates the estimated value by dynamic programming.

20. The ultrasonic diagnostic apparatus of claim 19, wherein the boundary estimating section calculates the estimated value by using an intensity distribution with a decreased resolution from an original resolution, and wherein the boundary defining section tentatively chooses candidates based on the intensity distribution with the decreased resolution and then defines the lumen boundary and the adventitia boundary in a region surrounding the tentatively chosen candidates based on the intensity distribution with the original resolution.

21. The ultrasonic diagnostic apparatus of claim 19, wherein the boundary estimating section calculates the estimated value in an acoustic line direction with the candidates narrowed down, by dynamic programming, to ones that have either good estimated values or a predetermined estimated value.

22. The ultrasonic diagnostic apparatus of claim 19, wherein the boundary continuity calculating section calculates the degree of continuity between boundaries, which is defined by a level difference between the boundaries in an acoustic line direction.

23. The ultrasonic diagnostic apparatus of claim 19, wherein the pattern similarity calculating section, the boundary continuity calculating section, the boundary estimating section and the boundary defining section screen potential boundary candidates for the lumen boundary and the adventitia boundary, and wherein the boundary defining section defines the lumen boundary and the adventitia boundary at the same time.

24. The ultrasonic diagnostic apparatus of claim 19, wherein the boundary continuity calculating section calculates the degree of continuity between the boundaries, which is defined as a thickness difference to be determined by the levels of the lumen and adventitia boundaries in an acoustic line direction.

25. The ultrasonic diagnostic apparatus of claim 19, wherein if the pattern similarity calculating section calculates the degree of similarity while the boundary defining section is setting the lumen and adventitia boundaries in a predetermined order and when the level of one of the two boundaries has not been determined yet, the pattern similarity calculating section fixes the other boundary, calculates the degrees of similarity with respect to a template that has multiple thicknesses associated with the level of the one boundary, and defines either the maximum value or the average value of the degrees of similarity calculated to be the degree of similarity of the other boundary.

26. The ultrasonic diagnostic apparatus of claim 19, wherein the boundary defining section compares an estimated value that has been used to detect a lumen boundary and then an adventitia boundary with the candidates narrowed down to ones under the lumen boundary to an estimated value that has been used to detect the adventitia boundary and then the lumen boundary with the candidates narrowed down to ones over the adventitia boundary, and finally adopts a boundary that has been detected with a better estimated value.

27. A method for measuring the intima-media thickness of a vascular wall based on an echo signal that has been received from a body in response to a ultrasonic wave that has been transmitted toward him or her, the method comprising the steps of:

generating an echo intensity distribution in a depth direction with respect to the vascular wall based on the echo signal;

generating a template for use to detect a boundary based on template data that has been provided in advance to represent a reference pattern of the echo intensity distribution;

changing, in combination, the level of the template in the depth direction and a pattern of the template representing the intima-media thickness to calculate the degree of similarity between the template and the intensity distribution on any change made in the level or pattern of the template;

defining a lumen boundary and an adventitia boundary based on the degree of similarity that has been calculated on any change made in the level or pattern of the template; and calculating the intima-media thickness based on the lumen and adventitia boundaries that have been defined.

28. A method for measuring the intima-media thickness of a vascular wall based on an echo signal that has been received from a body in response to a ultrasonic wave that has been transmitted toward him or her, the method comprising the steps of:

generating an echo intensity distribution in a depth direction with respect to the vascular wall based on the echo signal;

generating a template for use to detect a boundary based on template data that has been provided in advance to represent a reference pattern of the echo intensity distribution;

changing, in combination, a pattern of the template representing the intima-media thickness for each of multiple different combinations of candidate boundaries that are located at mutually different levels in the depth direction to calculate the degree of similarity between the template and the intensity distribution on any change made in the pattern of the template;

calculating, with respect to the combination selected in association with multiple adjacent acoustic lines, the degree of continuity between the boundaries based on a difference between intensity values of the echo signals of the respective acoustic lines;

generating an estimated value by integrating together the pattern similarity and the boundary continuity with respect to the combination;

defining a lumen boundary and an adventitia boundary based on the integrated estimated value; and calculating the intima-media thickness based on the lumen and adventitia boundaries that have been defined.

* * * * *